(12) United States Patent
Ohsaka et al.

(10) Patent No.: US 11,834,642 B2
(45) Date of Patent: Dec. 5, 2023

(54) COLLECTION METHOD FOR FINE PARTICLES AND COLLECTION SYSTEM

(71) Applicant: TOKYO OHKA KOGYO CO., LTD., Kawasaki (JP)

(72) Inventors: Takashi Ohsaka, Kawasaki (JP); Yasuo Suzuki, Kawasaki (JP); Atsushi Murota, Kawasaki (JP)

(73) Assignee: Tokyo Ohka Kogyo Co., Ltd., Kawasaki (JP)

( * ) Notice: Subject to any disclaimer, the term of this patent is extended or adjusted under 35 U.S.C. 154(b) by 1082 days.

(21) Appl. No.: 16/335,123

(22) PCT Filed: Sep. 21, 2017

(86) PCT No.: PCT/JP2017/034082
§ 371 (c)(1),
(2) Date: Mar. 20, 2019

(87) PCT Pub. No.: WO2018/061973
PCT Pub. Date: Apr. 5, 2018

(65) Prior Publication Data
US 2019/0225927 A1    Jul. 25, 2019

(30) Foreign Application Priority Data

Sep. 29, 2016   (JP) ................................ 2016-191451

(51) Int. Cl.
*C12M 1/00* (2006.01)
*G01N 1/04* (2006.01)
(Continued)

(52) U.S. Cl.
CPC .............. *C12M 29/06* (2013.01); *C12M 1/00* (2013.01); *C12M 1/32* (2013.01); *C12M 23/04* (2013.01);
(Continued)

(58) Field of Classification Search
CPC ........ C12M 23/04; C12M 29/06; C12M 1/00; C12M 33/04; C12M 23/20; C12M 1/32;
(Continued)

(56) References Cited

U.S. PATENT DOCUMENTS

2005/0277125 A1\* 12/2005 Benn .................... B01J 19/0046
435/287.2
2006/0164479 A1\* 7/2006 Takagi ................. B41J 2/17513
347/85

(Continued)

FOREIGN PATENT DOCUMENTS

EP          2908116 A1     8/2015
JP        2007-222132 A    9/2007
(Continued)

OTHER PUBLICATIONS

Concave. (2007). In R. E. Allen (Ed.), The penguin English Dictionary (3rd ed.). Penguin. Credo Reference: https://search.credoreference.com/content/entry/penguineng/concave/0?institutionId=743 (Year: 2007).\*

(Continued)

*Primary Examiner* — Sean C. Barron
(74) *Attorney, Agent, or Firm* — Knobbe, Martens, Olson & Bear, LLP

(57) ABSTRACT

A method for collecting a fine particle stored in a structure by suctioning the fine particle using a nozzle, in which, as the structure, a structure in which at least one communication portion that communicates a space storing the fine particle with one surface side and the other surface side of the structure is formed is used.

3 Claims, 12 Drawing Sheets

(51) Int. Cl.
    *C12M 1/26* (2006.01)
    *C12M 1/12* (2006.01)
    *C12M 1/32* (2006.01)
    *G01N 1/02* (2006.01)
    *C12Q 1/02* (2006.01)

(52) U.S. Cl.
    CPC ............ *C12M 23/20* (2013.01); *C12M 33/04* (2013.01); *C12Q 1/02* (2013.01); *G01N 1/02* (2013.01); *G01N 1/04* (2013.01); *C12M 23/12* (2013.01)

(58) Field of Classification Search
    CPC . C12M 23/12; G01N 1/04; G01N 1/02; B01L 3/021; B01L 3/50; C12Q 1/02
    See application file for complete search history.

(56) References Cited

U.S. PATENT DOCUMENTS

2006/0257999 A1* 11/2006 Chang ..................... C40B 60/06
                                                                    435/289.1
2016/0312164 A1   10/2016 Ito
2016/0348066 A1   12/2016 Kuchiishi et al.
2018/0282677 A1   10/2018 Ohsaka et al.

FOREIGN PATENT DOCUMENTS

| JP | 2010-200714 A | 9/2010 |
| JP | 5625125 B | 11/2014 |
| JP | 2016-093149 A | 5/2016 |
| WO | WO 2015/087369 A1 | 6/2015 |
| WO | WO 2016/046938 A1 | 3/2016 |
| WO | WO 2017/057234 A1 | 4/2017 |
| WO | WO 2017/110005 A1 | 6/2017 |

OTHER PUBLICATIONS

International Search Report issued in International Application No. PCT/JP2017/034082, dated Dec. 19, 2017.
Office Action in Korean Patent Application No. 10-2019-7008417 dated Sep. 1, 2021.
Search Report issued in European Patent Application No. 17855928.2, dated Apr. 20, 2020.

* cited by examiner

COLLECTION METHOD FOR FINE PARTICLES AND COLLECTION SYSTEM

BACKGROUND OF THE INVENTION

Field of the Invention

The present invention relates to a collection method for fine particles and a collection system.

Priority is claimed on Japanese Patent Application No. 2016-191451, filed on Sep. 29, 2016, the content of which is incorporated herein by reference.

Description of Related Art

In the related art, a screening device of fine particles is known (for example, refer to Japanese Patent No. 5625125). This screening device includes a measuring chip in which wells storing fine particles are formed and a collection portion which has a capillary, absorbs the fine particles in the wells, ejects the fine particles to a predetermined location, and collects the fine particles. On the upper surface of the measuring chip, a number of wells having cup-like concave shapes are arranged in a matrix form. In order to realize the accurate suction operation of the fine particles, the distances between the capillary and the wells are set to be smaller than the diameters of the fine particles.

SUMMARY OF THE INVENTION

When an attempt is made to collect fine particles in a measuring chip in which wells having cup-like concave shapes are formed, if the tip of the capillary and the upper surface of the measuring chip are brought into contact with each other (adhered to each other), there is a possibility that it may not be possible to produce the flow of intake air which has engulfed the fine particles. That is, the flow of the intake air is blocked at the contact portion between the tip of the capillary and the upper surface of the measuring chip, and thus there is a possibility that it may not be possible to suction the fine particles. Therefore, there is a possibility that it may not be possible to reliably suction desired fine particles.

The present invention has been made in consideration of the above-described problems, and an object of the present invention is to provide a collection method for fine particles and a collection system which are capable of reliably suctioning desired a fine particle.

A collection method for fine particles according to a first aspect of the present invention is a method for collecting a fine particle stored in a structure by suctioning the fine particle using a nozzle, in which, as the structure, a structure in which at least one communication portion that communicates a space storing the fine particle with one surface side and the other surface side of the structure is formed is used.

According to this method, it is possible to produce the flow of intake air which has engulfed a fine particle in the communication portion, and thus a desired fine particle can be reliably suctioned.

In the collection method for fine particles, as the structure, a substrate in which at least one concave portion that sinks so as to be capable of storing the fine particle are formed on one surface side and at least one communication hole which communicates with an inner wall of the concave portion and the other surface side and has a hole diameter that is smaller than the size of the fine particle are formed may be used.

According to this method, it is possible to produce the flow of intake air which has engulfed a fine particle between the concave portion and the communication hole in the substrate, and thus a desired fine particle can be reliably suctioned. Additionally, the communication hole has a hole diameter that is smaller than the size of the fine particle, and thus the fine particle does not pass through the communication hole, and the fine particle can be reliably held in the concave portion.

In the collection method for fine particles, as the structure, a substrate in which at least one through-hole penetrating the substrate so as to be capable of storing the fine particle is formed and a support portion capable of supporting the fine particle is formed in an inner wall of the through-hole may be used.

According to this method, it is possible to produce the flow of intake air which has engulfed a fine particle through the through-hole in the substrate, and thus a desired fine particle can be reliably suctioned. Additionally, the support portion capable of supporting the fine particle is formed in the inner wall of the through-hole, and thus the fine particle does not pass through the through-hole, and the fine particle can be reliably held in the support portion.

In the collection method for fine particles, as the structure, a structure including a substrate in which at least one through-hole penetrating the structure so as to be capable of storing the fine particle is formed and a support layer which is disposed on the other surface side of the substrate, has at least one communication hole that communicates with the through-hole, and is capable of supporting the fine particle may be used.

According to this method, it is possible to produce the flow of intake air which has engulfed a fine particle between the through-hole in the substrate and the communication hole in the support layer, and thus a desired fine particle can be reliably suctioned.

In the collection method for fine particles, the structure may include a support layer which has at least one concave portion that sink so as to be capable of storing the fine particle, has at least one communication hole that communicates with the concave portion, and is capable of supporting the fine particle and a coating layer that covers a surface of the support layer on the concave portion side.

According to this method, it is possible to produce the flow of intake air which has engulfed a fine particle between the concave portion and the communication hole in the support layer, and thus a desired fine particle can be reliably suctioned. Additionally, the coating layer covers the surface of the support layer on the concave portion side, it is possible to suppress the intrusion of foreign substances into the communication hole in the support layer.

In the collection method for fine particles, the fine particle may be suctioned and collected using the nozzle in a state in which the nozzle is in contact with one surface of the structure.

According to this method, it is possible to avoid the suction of external foreign substances compared with a case in which the nozzle is away from one surface of the structure. Therefore, it is possible to avoid contamination with foreign substances and reliably suction a desired fine particle. Additionally, it is possible to produce the flow of intake air which has engulfed a fine particle only between the through-hole in the substrate and the communication hole in the support layer, and it is possible to suppress the suction power of the nozzle at a lower level compared with a case in which the nozzle is away from one surface of the structure.

A collection system according to a second aspect of the present invention is a collection system including a structure capable of storing at least one fine particle and a nozzle suctioning and collecting the fine particle stored in the structure, in which, in the structure, a communication portion that communicates a space storing the fine particle with one surface side and the other surface side of the structure is formed.

According to this constitution, it is possible to produce the flow of intake air which has engulfed a fine particle in the communication portion, and thus desired fine particles can be reliably suctioned.

In the collection system, the structure may be a substrate in which at least one concave portion that sinks so as to be capable of storing the fine particle is formed on one surface side and a communication hole which communicates with an inner wall of the concave portion and the other surface side and has a hole diameter that is smaller than the size of the fine particle is formed.

According to this constitution, it is possible to produce the flow of intake air which has engulfed a fine particle between the concave portion and the communication hole in the substrate, and thus a desired fine particle can be reliably suctioned. Additionally, the communication hole has a hole diameter that is smaller than the size of the fine particle, and thus the fine particle does not pass through the communication hole, and the fine particle can be reliably held in the concave portion.

In the collection system, the structure may be a substrate in which at least one through-hole penetrating the substrate so as to be capable of storing the fine particle is formed and a support portion capable of supporting the fine particle is formed in an inner wall of the through-hole.

According to this constitution, it is possible to produce the flow of intake air which has engulfed a fine particle through the through-hole in the substrate, and thus a desired fine particle can be reliably suctioned. Additionally, the support portion capable of supporting the fine particle is formed in the inner wall of the through-hole, and thus the fine particle does not pass through the through-hole, and the fine particle can be reliably held in the support portion.

In the collection system, the structure may include a substrate in which at least one through-hole penetrating the substrate so as to be capable of storing the fine particle is formed and a support layer which is disposed on the other surface side of the substrate, has at least one communication hole that communicates with the through-hole, and is capable of supporting the fine particle.

According to this constitution, it is possible to produce the flow of intake air which has engulfed a fine particle between the through-hole in the substrate and the communication hole in the support layer, and thus a desired fine particle can be reliably suctioned.

In the collection system, the structure may include a support layer which has at least one concave portion that sink so as to be capable of storing the fine particle, has at least one communication hole that communicates with the concave portion, and is capable of supporting the fine particle and a coating layer that covers a surface of the support layer on the concave portion side.

According to this constitution, it is possible to produce the flow of intake air which has engulfed a fine particle between the concave portion and the communication hole in the support layer, and thus a desired fine particle can be reliably suctioned. Additionally, the coating layer covers the surface of the support layer on the concave portion side, it is possible to suppress the intrusion of foreign substances into the communication hole in the support layer.

In the collection system, the structure may include a first substrate in which at least one through-hole penetrating the substrate so as to be capable of storing the fine particle is formed, a second substrate facing the first substrate, and a support layer which is disposed between the first substrate and the second substrate, has at least one communication hole that communicates with the through-hole, and is capable of supporting the fine particle.

According to this constitution, it is possible to produce the flow of intake air which has engulfed a fine particle between the through-hole in the first substrate and the communication hole in the support layer. Therefore, a desired fine particle can be reliably collected.

According to the present invention, it is possible to provide a collection method for fine particles and a collection system which are capable of reliably suctioning a desired fine particle.

DETAILED DESCRIPTION OF THE INVENTION

Hereinafter, embodiments of the present invention will be described with reference to the accompanying drawings.

In the following description, the XYZ orthogonal coordinate is set, and the locational relationships of individual members will be described with reference to this XYZ orthogonal coordinate. A predetermined direction in the horizontal plane will be considered as an X-axis direction, a direction perpendicular to the X-axis direction in the horizontal plane will be considered as a Y-axis direction, and a direction that is respectively perpendicular to the X-axis direction and the Y-axis direction (that is, a vertical direction) will be considered as a Z-axis direction. In addition, the rotation directions around the X axis, the Y axis, and the Z axis will be respectively considered as θX, θY, and θZ directions.

First Embodiment

Hereinafter, a first embodiment of the present invention will be described using FIG. 1 to FIG. 7. In the present embodiment, a collection system that is used in a collection method for fine particles in which fine particles stored in a structure are suctioned and collected using a nozzle will be described as an example. A collection system of the present embodiment includes a structure capable of storing fine particles and a nozzle suctioning and collecting the fine particles stored in the structure. The structure in the present embodiment is a substrate in which concave portions capable of storing fine particles are formed on one surface side and communication holes which communicate with inner walls of the concave portions and the other surface side and have hole diameters that are smaller than sizes of the fine particles are formed.

For example, the fine particles are cells having diameters of approximately 10 μm to 200 μm. Examples of the cells include antibody-secreting cells, rare cells, and the like. The concept of "fine particles" is not limited to single cells, but broadly includes colonies and spheroids (clusters of cells).

For example, the collection system selectively collects target cells. The concept of "collection" is not limited to the selective collection of target cells but broadly includes cases in which cells are moved into separate containers and collected.

<Collection System>

Figure 1:
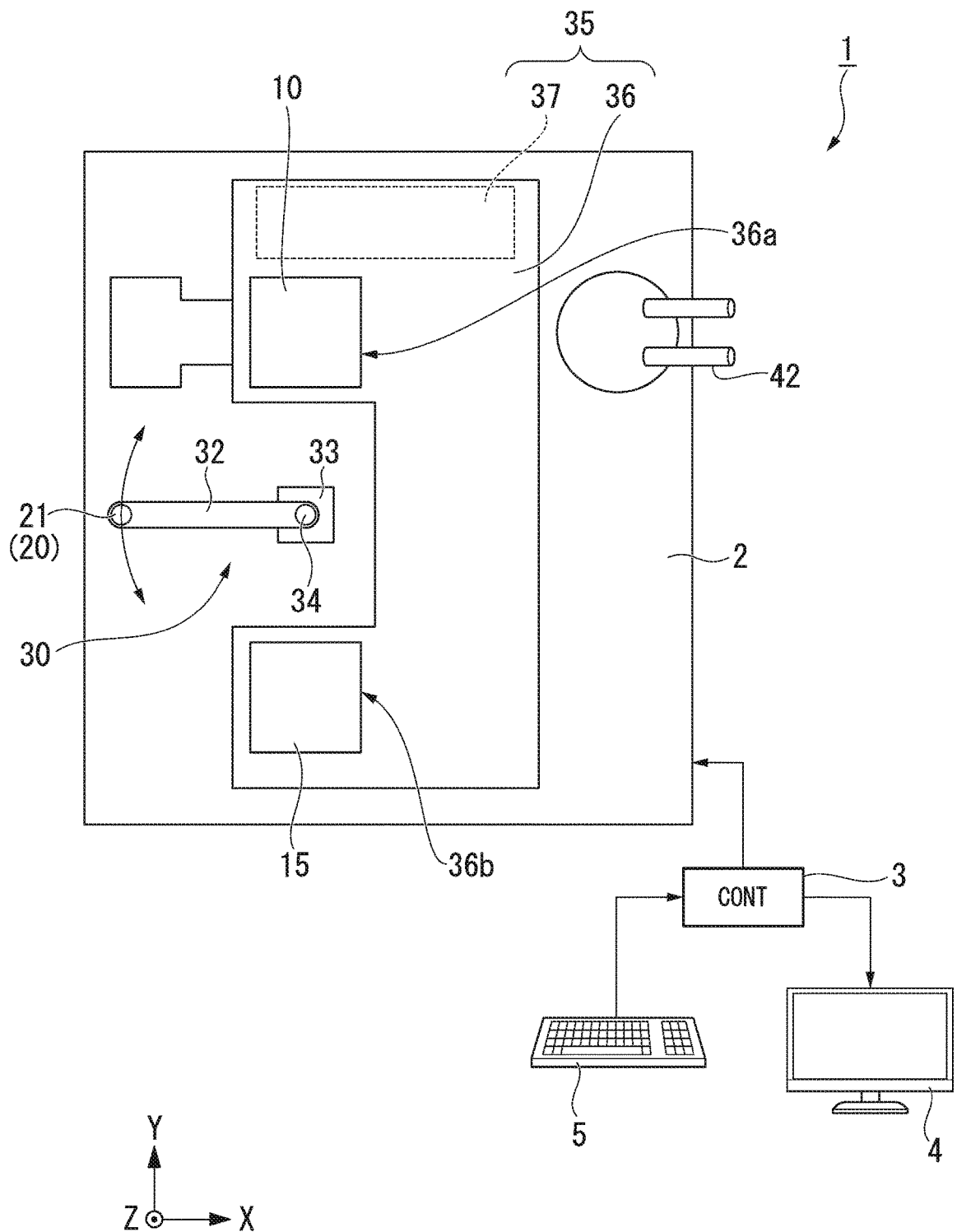
FIG. 1 is a plan view illustrating a schematic constitution of a collection system according to a first embodiment.

FIG. 1 is a plan view illustrating the schematic constitution of a collection system 1 according to the first embodiment.

As illustrated in FIG. 1, the collection system 1 includes a base 2, a control device 3, a display device 4, an input device 5, a substrate 10 (structure), a nozzle 20, and a nozzle location measurement device 30. The collection system 1 is covered with a non-illustrated case. Therefore, the intrusion of foreign substances (grit and dust) into the collection system 1 from the outside is prevented.

<Base>

The base 2 holds the respective elements (the substrate 10, the nozzle 20, and the nozzle location measurement device 30) of the collection system 1. In a planar view, the base 2 has a rectangular shape.

<Control Device>

The control device 3 controls the driving of the respective elements (the nozzle 20 and the nozzle location measurement device 30) of the collection system 1.

<Display Device>

The display device 4 displays letters and images. The display device 4 displays a variety of information regarding the collection system 1. For example, the display device 4 is a liquid crystal display.

<Input Device>

The input device 5 includes an input instrument that receives the operation of operators. For example, the input instrument is a keyboard, a mouse, or the like. The input device 5 outputs information that has been input to the control device 3.

<Substrate (Structure)>

Figure 2:
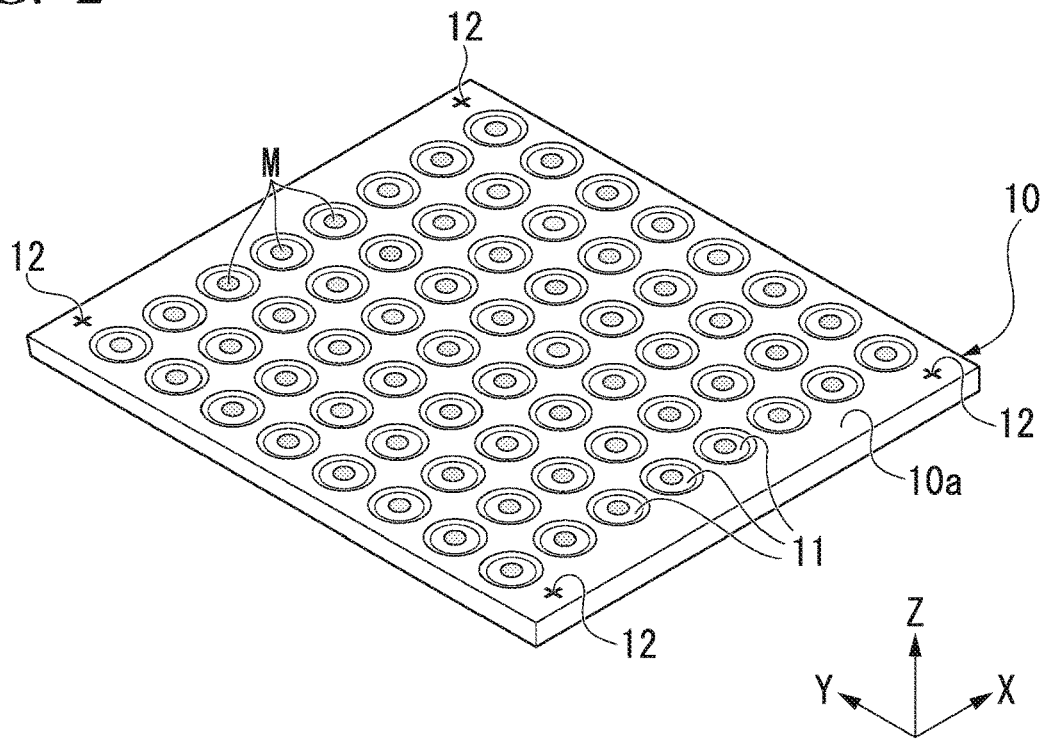
FIG. 2 is a perspective view illustrating a schematic constitution of a substrate.

FIG. 2 is a perspective view illustrating the schematic constitution of the substrate 10.

As illustrated in FIG. 2, the substrate 10 has a rectangular sheet shape. For example, the substrate 10 has lengths of approximately 50 mm in the X-axis direction and the Y-axis direction. The substrate 10 is light-transmissible. For example, the substrate 10 is a glass substrate or a plastic substrate.

In the substrate 10, a plurality of concave portions 11 that sink so as to be capable of storing fine particles M is formed. The plurality of concave portions 11 is disposed in a matrix form along the X-axis direction and the Y-axis direction at certain intervals. For example, the cross-sectional shape of the concave portion 11 forms a U-like concave shape or a cup-like concave shape. The size of the concave portion 11 may be a size in which only one fine particle M can be stored. Therefore, it is possible to rapidly collect a single kind of target cells or the like. The size of the concave portion 11 may be a size in which a plurality of fine particles M can be stored and is not particularly limited.

Figure 6:
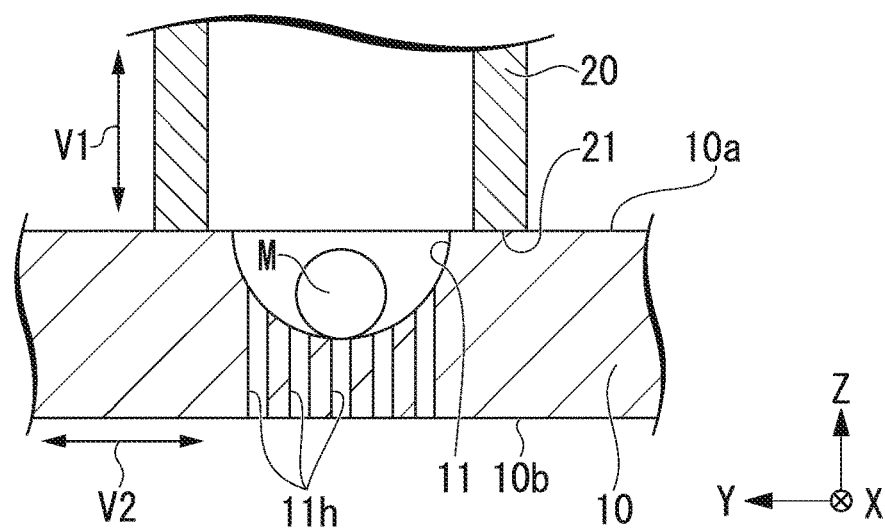
FIG. 6 is a view illustrating a state in which a tip portion of a nozzle is in contact with a front surface of the substrate.

In the substrate 10, a plurality of communication holes 11h communicating with bottom walls (inner walls) of the concave portions 11 and a rear surface 10b side (the other surface side) is formed (refer to FIG. 6). The concave portions 11 and the communication holes 11h communicate spaces storing the fine particles M with one surface side and the other surface side of the substrate 10. The concave portions 11 and the communication holes 11h correspond to "communication portions". The communication holes 11h linearly extend toward the rear surface 10b from the bottom walls of the concave portions 11. The communication holes 11h have hole diameters that are smaller than the sizes of the fine particles M.

In the respective concave portions 11, a culture solution is stored together with the fine particles M. Examples of the culture solution include DMEM culture media, MEM culture media, RPMI 1640 culture media, Fischer's culture media, and the like. The kind of culture solution is not particularly limited.

In the corner portions of a front surface 10a (upper surface) of the substrate 10, markings 12 are formed. The markings 12 serve as references for setting the coordinates of the respective concave portions 11 with respect to the X-axis direction and the Y-axis direction on the front surface 10a of the substrate 10. For example, the markings 12 are formed by cutting the corner portions of the front surface 10a of the substrate 10. The markings 12 may be formed by printing the markings on the corner portions of the front surface 10a of the substrate 10.

<Nozzle>

Figure 3:
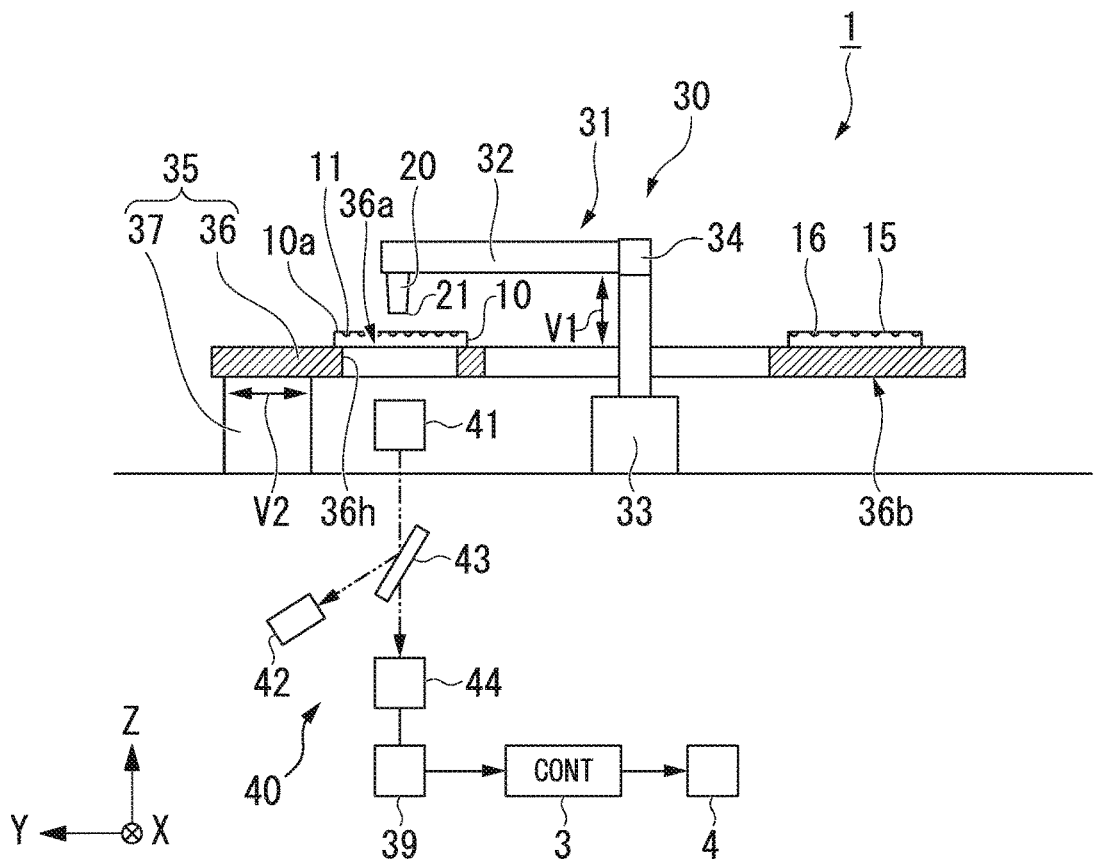
FIG. 3 is a view illustrating a main portion of the collection system according to the first embodiment.

FIG. 3 is a view illustrating the main portion of the collection system 1 according to the first embodiment.

As illustrated in FIG. 3, the nozzle 20 has a tubular shape that tapers downwards in the Z-axis direction. For example, the nozzle 20 is formed of a resin or metal. For example, the nozzle 20 is a microcapillary. As the nozzle 20, a nozzle having a size appropriate to the size of the concave portion 11 in the substrate 10 is used. For example, the inner diameter of a tip portion 21 of the nozzle 20 is set to approximately twice the diameter of the concave portion 11. For example, the inner diameter of a tip portion 21 of the nozzle 20 reaches approximately 10 μm to 100 μm.

A suction pump (not illustrated) is connected to the nozzle 20. For example, the suction pump is a tube pump that is driven using a stepping motor. When the suction pump rotates clockwise, the nozzle 20 suctions the fine particle M through the tip portion 21. On the other hand, when the suction pump rotates counterclockwise, the nozzle 20 discharges the fine particle M through the tip portion 21.

<Nozzle Location Measurement Device>

The nozzle location measurement device 30 measures the location of the nozzle 20 with respect to the substrate 10. The nozzle location measurement device 30 includes a nozzle-lifting-and-lowering mechanism 31, a structure-moving mechanism 35, a determination portion 39, and a camera 40.

<Nozzle-Lifting-and-Lowering Mechanism>

The nozzle-lifting-and-lowering mechanism 31 lifts and lowers the nozzle 20 with respect to the substrate 10 in a first direction V1. The "first direction" corresponds to the normal direction (for example, the Z-axis direction) of the front surface 10a of the substrate 10. The nozzle-lifting-and-lowering mechanism 31 includes an arm 32, a Z driving mechanism 33, and a nozzle location-adjusting mechanism 34.

The arm 32 holds the nozzle 20. The arm 32 is a rod-shaped member extending in a direction parallel to the XY plane. The nozzle 20 is detachably attached to one end portion of the arm 32. The Z driving mechanism 33 is coupled with the other end portion of the arm 32.

The Z driving mechanism 33 enables the arm 32 to be lifted and lowered in the Z-axis direction and is capable of rotating around the Z axis (in a θZ direction). For example, the Z driving mechanism 33 is driven using a stepping motor. The above-described constitution enables the nozzle 20 to execute operations such as turning, lifting and lowering, suctioning, and discharging.

For example, for the Z driving mechanism 33, the stroke in the Z-axis direction is set to 20 mm, the movement rate is set to 5 to 5,000 μm/sec, and the location control in the Z-axis direction is set to ±1 μm. In addition, for the Z driving mechanism 33, in the turning operation in the θZ direction, the driving angle is set to ±100 degrees (stroke: 200 degrees), and the rotation location control is set to ±0.002 degrees.

The nozzle location-adjusting mechanism 34 is a mechanism for aligning the nozzle 20. For example, the nozzle location-adjusting mechanism 34 includes a knob for adjustment such as a micrometer. Therefore, it is possible to finely adjust the attachment location of the nozzle 20 with respect to the arm 32 in the XY plane.

<Structure-moving mechanism>

The structure-moving mechanism 35 moves the substrate 10 in a second direction V2 that intersects the first direction V1. The "second direction" corresponds to a direction (for example, the X-axis direction or the Y-axis direction) orthogonal to the normal direction of the front surface 10a of the substrate 10. The structure-moving mechanism 35 includes a stage 36 and an XY driving mechanism 37.

The stage 36 is a mounting table on which the substrate 10 is mounted. On the upper surface of the stage 36, a suction and collection region 36a and a discharge and collection region 36b are provided. The suction and collection region 36a is a region for carrying out a collection operation in which the fine particles M are suctioned and collected from the concave portions 11 in the substrate 10. The discharge and collection region 36b is a region for discharging and collecting the fine particles M suctioned and collected from the concave portions 11 in the substrate 10. That is, the nozzle 20 suctions the fine particles M from the substrate 10 (the concave portions 11) in the suction and collection region 36a and discharges the suctioned fine particles M in the discharge and collection region 36b.

In the discharge and collection region 36b, a collection tray 15 for collecting the fine particles M discharged from the nozzle 20 is installed. The collection tray 15 has a rectangular sheet shape. In the collection tray 15, a plurality of wells 16 that sink so as to be capable of storing the fine particles M is formed. The plurality of wells 16 is disposed in a matrix form along the X-axis direction and the Y-axis direction at certain intervals. The wells 16 separately collect and store the fine particles M that are sequentially discharged from the nozzle 20. For example, the cross-sectional shape of the well 16 forms a U-like concave shape or a cup-like concave shape. The size of the well 16 may be approximately the same as the size of the concave portion 11 in the substrate 10. The size of the well 16 may be a size in which the plurality of fine particles M can be stored and is not particularly limited.

In the suction and collection region 36a in the stage 36, an opening 36h facing the lower surface of the substrate 10 is formed. In the suction and collection region 36a in the stage 36, a guide (not illustrated) for holding the substrate 10 is provided. Therefore, the substrate 10 is held in a state of being located at a predetermined location in the suction and collection region 36a.

The method for holding the substrate 10 in the suction and collection region 36a may be adsorption holding using an adsorption mechanism and is not particularly limited.

The XY driving mechanism 37 is capable of moving the stage 36 in the X-axis direction and the Y-axis direction. For example, the XY driving mechanism 37 includes a motor, a reed screw, and the like. The XY driving mechanism 37 may include a linear motor or the like and is not particularly limited.

The structure-moving mechanism 35, separately from the XY driving mechanism 37, may be capable of inclining the upper surface of the stage 36 in the XY plane. In such a case, even in a case in which there is a slight slope in the parallelism of the front surface 10a of the substrate 10, the stage 36 is capable of correcting the slope.

<Determination Portion>

The determination portion 39 is connected to the control device 3. The determination portion 39 determines whether or not the nozzle 20 moves together with the substrate 10 when the substrate 10 is moved in the second direction V2.

<Camera>

The camera 40 captures the nozzle 20 with the focus adjusted to the front surface 10a of the substrate 10. The camera 40 includes a zoom lens 41, an eye lens 42, a half mirror 43, and a light reception portion 44.

The zoom lens 41 is disposed in a state of facing the lower surface of the substrate 10 through the opening 36h formed in the suction and collection region 36a.

The zoom lens 41 adjusts the focus to the front surface 10*a* of the substrate 10. Therefore, the camera 40 has a focus adjusted to the front surface 10*a* of the substrate 10.

The eye lens 42 makes observation images visible to the eyes of operators through the zoom lens 41.

The half mirror 43 is disposed on a light path between the zoom lens 41 and the light reception portion 44. The half mirror 43 transmits a part of light that has passed through the zoom lens 41 and reflects the remaining part. The light reflected by the half mirror 43 is guided to the eye lens 42.

For example, the light reception portion 44 is a capturing element such as a CCD image sensor. The light reception portion 44 outputs captured images to the control device 3 through the determination portion 39. Therefore, the display device 4 displays the captured images of the camera 40.

Figure 4:
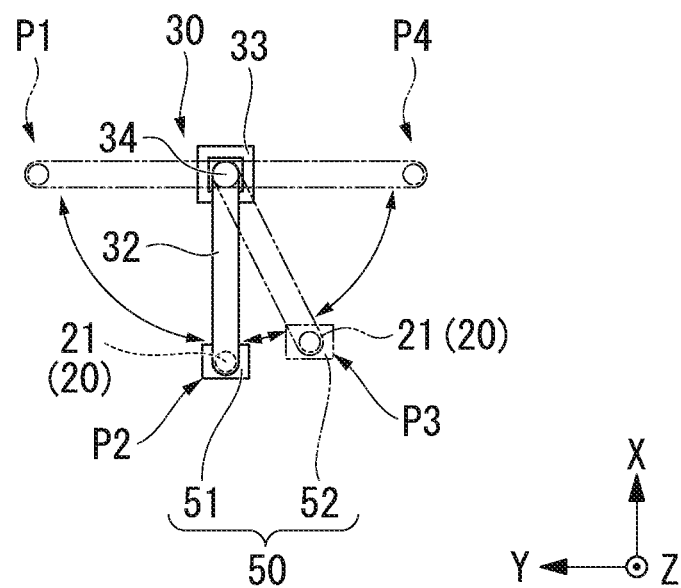
FIG. 4 is a plan view illustrating a schematic constitution of a dipping portion.

FIG. 4 is a plan view illustrating the schematic constitution of a dipping portion 50.

As illustrated in FIG. 4, the collection system 1 of the embodiment further includes the dipping portion 50 that immerses (dips) the nozzle 20. The dipping portion 50 includes a reagent-dipping portion 51 and a wash solution-dipping portion 52.

Hereinafter, the location in which the nozzle 20 suctions the fine particle M will be referred to as "suction position", the waiting location of the nozzle 20 will be referred to as "waiting position (home position)", the location in which the nozzle 20 is washed will be referred to as "washing position", and the location in which the nozzle 20 discharges the fine particle M will be referred to as "discharge position". The nozzle 20 moves among a suction position P1, a waiting position P2, a washing position P3, and a discharge position P4 by the revolution operation of the arm 32.

The reagent-dipping portion 51 is disposed in the waiting position P2. The reagent-dipping portion 51 causes the tip portion 21 of the nozzle 20 to be in a state of being wetted by liquid. Therefore, it is possible to suppress the tip portion 21 of the nozzle 20 being dried in the waiting position P2.

In the reagent-dipping portion 51, as liquid in which the tip portion 21 of the nozzle 20 is dipped, for example, the culture solution that is disposed in the concave portions 11 together with the fine particles M or phosphate buffered saline (PBS) is used.

The wash solution-dipping portion 52 is disposed in the washing position P3. The wash solution-dipping portion 52 washes the inside of the tip portion 21 of the nozzle 20 by filling the tip portion 21 of the nozzle 20 with a wash solution. Therefore, even in a case in which one nozzle 20 is commonly used for fine particle collection operations in the respective concave portions 11, it is possible to suppress the occurrence of contamination.

In the wash solution-dipping portion 52, as the wash solution that washes the tip portion 21 of the nozzle 20, for example, the culture solution that is disposed in the concave portions 11 together with the fine particles M or phosphate-buffered saline (PBS) is used.

<Collection Method for Fine Particles>

Hereinafter, an example of a collection method for fine particles in which the fine particles M stored in the concave portions 11 in the substrate 10 are suctioned and collected using the nozzle 20 in the collection system 1 of the present embodiment will be described.

The collection method for fine particles of the present embodiment is a method in which the fine particles M are suctioned and collected using the nozzle 20 in a state in which the interval between the nozzle 20 and the substrate 10 is set to be smaller than the sizes of the fine particles M.

The collection method for fine particles of the present embodiment includes a nozzle location measurement step before the suction and collection of the fine particles M using the nozzle 20. The nozzle location measurement step is a step in which the location of the nozzle 20 with respect to the substrate 10 is measured using the collection system 1 of the present embodiment.

Specifically, the nozzle location measurement step includes a nozzle lifting and lowering step of lifting and lowering the nozzle 20 with respect to the substrate 10 in the first direction V1, a substrate moving step of moving the substrate 10 in the second direction V2 after the nozzle lifting and lowering step, and a determination step of determining whether or not the nozzle 20 moves together with the substrate 10 in the substrate moving step.

First, the power supply of the collection system 1 is turned on.

When the power supply is turned on, the collection system 1 carries out an initialization operation. For example, in the initialization operation, the stage 36 is moved to a waiting location (initial location). In addition, after the turning operation, lifting and lowering operation, and suction and discharge operation of the nozzle 20, the nozzle 20 is moved to the waiting location (the waiting position P2). Therefore, it is possible to confirm that the stage 36 and the nozzle 20 normally operate without interfering other mechanisms. Additionally, a state in which the stage 36 and the nozzle 20 are waiting in the reference location (the home position) is formed.

Next, the substrate 10 storing the fine particles M in the respective concave portions 11 is set in the suction and collection region 36*a* of the stage 36. In addition, the collection tray 15 is set in the discharge and collection region 36*b* of the stage 36. For example, the setting operation of the substrate 10 and the collection tray 15 is manually carried out by operators. The setting operation may be automatized using robots.

Next, the locations of the substrate 10 and the nozzle 20 in the X-axis direction and the Y-axis direction are determined (hereinafter, referred to as "XY alignment"). For example, the XY alignment is visually carried out. Specifically, the XY alignment is carried out by moving the stage 36 in the X-axis direction and the Y-axis direction using the XY driving mechanism 37 while visually confirming the tip portion 21 of the nozzle 20 so as to overlap the concave portions 11 in the Z-axis direction. Additionally, the XY alignment is carried out by operating the knob for adjustment (micrometer) in the nozzle location-adjusting mechanism 34.

For example, in the XY alignment, a non-illustrated lower side illumination is turned on, and the location in the XY plane of the nozzle 20 at the suction position P1 is determined. At this time, the illumination light passes through the concave portions 11 and reaches the nozzle 20. The light reflected by the nozzle 20 is guided to the eye lens 42 and the light reception portion 44 through the zoom lens 41 and the half mirror 43. In addition, the display device 4 displays images guided to the light reception portion 44 (the captured images of the camera 40).

Figure 5:
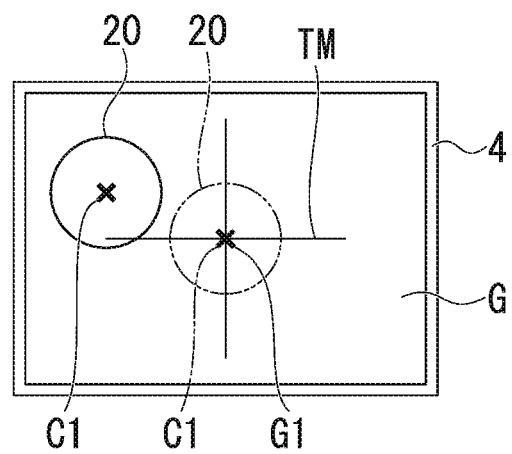
FIG. 5 is a view describing an XY alignment.

FIG. 5 is a view describing the XY alignment.

As illustrated in FIG. 5, in the XY alignment, for example, a central axis C1 (an axis passing through the radial direction center) of the nozzle 20 and a reference point G1 in an observation region of the concave portion 11 are matched. The "reference point G1 in an observation region of the concave portion 11" corresponds to the central point of a display image G (an image guided to the light reception portion 44) that is displayed on the display device 4.

The alignment of the central axis C1 of the nozzle 20 and the center G1 of the display image G is carried out by operating the knob for adjustment (micrometer) in the nozzle location-adjusting mechanism 34. For example, a target mark TM such as a cross mark is displayed at a location corresponding to the center G1 of the display region G Therefore, the alignment of the central axis C1 of the nozzle 20 and the center G1 of the display image G can be easily carried out.

Next, the focus is adjusted to the front surface 10a of the substrate 10. Specifically, in the nozzle lifting and lowering step, the tip portion 21 of the nozzle 20 is captured using the camera 40 having a focus adjusted to the front surface 10a of the substrate 10.

For example, in the focus adjustment, a non-illustrated upper side illumination is turned on. At this time, the illumination light passes through the concave portions 11 and is guided to the eye lens 42 and the light reception portion 44 through the zoom lens 41 and the half mirror 43. In addition, the display device 4 displays images guided to the light reception portion 44 (the captured images of the camera 40).

For example, the focus is adjusted to the front surface 10a of the substrate 10 while viewing the captured images of the camera 40 displayed on the display device 4.

The focus may be adjusted to the front surface 10a of the substrate 10 while viewing the observation images of the concave portions 11 through the eye lens 42.

Next, in the nozzle lifting and lowering step, the nozzle 20 is lowered in the first direction V1. Next, the in the substrate moving step, the substrate 10 is moved in the second direction V2. In addition, in the determination step, whether or not the nozzle 20 moves together with the substrate 10 is determined.

The tip portion 21 of the nozzle 20 has a tapering shape. Therefore, in a case in which the tip portion 21 of the nozzle 20 is in contact with the front surface 10a of the substrate 10 as illustrated in FIG. 6, the nozzle 20 is highly likely to move along the movement of the substrate 10. Therefore, when the nozzle 20 is determined as moving together with the substrate 10 in the determination step, it is possible to assume that the tip portion 21 of the nozzle 20 is in contact with the front surface 10a of the substrate 10.

Figure 7:
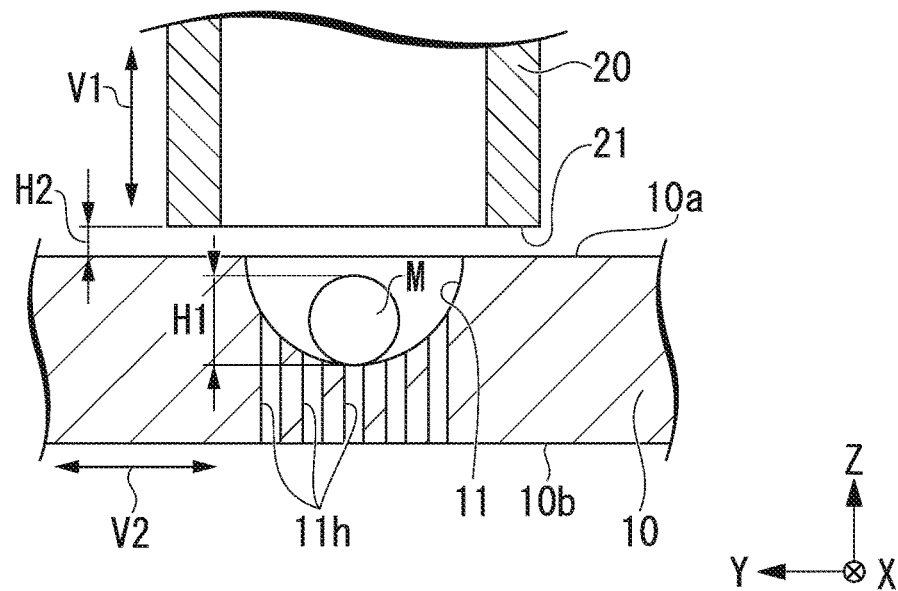
FIG. 7 is a view illustrating a state in which the tip portion of the nozzle is away from the front surface of the substrate.

On the other hand, in a case in which the tip portion 21 of the nozzle 20 is away from the front surface 10a of the substrate 10 as illustrated in FIG. 7, the nozzle 20 is highly unlikely to move along the movement of the substrate 10. Therefore, when the nozzle 20 is determined as not moving together with the substrate 10 in the determination step, it is possible to assume that the tip portion 21 of the nozzle 20 is away from the front surface 10a of the substrate 10.

The nozzle location measurement step in the present embodiment further includes a location-adjusting step of adjusting the relative locations of the nozzle 20 and the substrate 10 on the basis of the determination results in the determination step by moving the nozzle 20 away from the substrate 10 when the nozzle 20 has been determined as moving together with the substrate or resting the nozzle 20 when the nozzle 20 has been determined as not moving together with the substrate.

For example, in the location-adjusting step, when the nozzle 20 has been determined as moving together with the substrate on the basis of the determination results in the determination step, the nozzle 20 is moved away from the substrate 10 (hereinafter, referred to as "first adjustment").

In such a case, the state in which the tip portion 21 of the nozzle 20 is in contact with the front surface 10a of the substrate 10 is released. On the other hand, in the location-adjusting step, when the nozzle 20 has been determined as not moving together with the substrate on the basis of the determination results in the determination step, the nozzle 20 is rested (hereinafter, referred to as "second adjustment"). In such a case, the state in which the tip portion 21 of the nozzle 20 is away from the front surface 10a of the substrate 10 is maintained.

In addition, the relative locations of the nozzle 20 and the substrate 10 are adjusted on the basis of the determination results in the determination step. Specifically, after the first adjustment or the second adjustment, the nozzle 20 is slightly (for example, less than the movement amount in the nozzle lifting and lowering step) lowered in the first direction V1 (hereinafter, referred to as "third adjustment"). Next, after the third adjustment, whether or not the nozzle 20 moves together with the substrate 10 is determined by moving the substrate 10 in the second direction V2 (hereinafter, referred to as "fourth adjustment").

In the fourth adjustment, when the nozzle 20 has been determined as moving together with the substrate, the nozzle 20 is moved away from the substrate 10 (first adjustment). On the other hand, in the fourth adjustment, when the nozzle 20 has been determined as not moving together with the substrate on the basis of the determination results in the determination step, the nozzle 20 is rested (second adjustment). That is, in the location-adjusting step, the first adjustment through the fourth adjustment is repeated.

Therefore, in the location-adjusting step, the tip portion 21 of the nozzle 20 is moved as close as possible to the front surface 10a of the substrate 10. As illustrated in FIG. 7, in the location-adjusting step, the interval H2 between the tip portion 21 of the nozzle 20 and the front surface 10a of the substrate 10 is set to be smaller than the size H1 (diameter) of the fine particle M stored in the concave portion 11 in the substrate 10 (H2<H1). For example, in the location-adjusting step, in a case in which the size H1 of the fine particle M is approximately 10 µm, the interval H2 between the tip portion 21 of the nozzle 20 and the front surface 10a of the substrate 10 is set to approximately 1 µm.

Through the above-described steps, the nozzle location measurement step is completed. After the nozzle location measurement step, the fine particle M is suctioned and collected using the nozzle 20 in a state in which the interval H2 between the tip portion 21 of the nozzle 20 and the front surface 10a of the substrate 10 is set to be smaller than the size H1 of the fine particle M.

Therefore, compared with a case in which the interval H2 between the nozzle 20 and the substrate 10 is set to be equal to or larger than the size H1 of the fine particle M, the suction of external foreign substances can be suppressed. Additionally, even in constitutions in which a plurality of concave portions 11 capable of storing the fine particles M is formed in the substrate 10, it is possible to avoid the suction of the fine particles M stored in adjacent concave portions 11 by mistake when an attempt is made to suction the fine particle M stored in the target concave portion 11.

As described above, in the collection method for fine particles according to the present embodiment, as the structure, the substrate 10 in which the concave portions 11 that sink so as to be capable of storing the fine particles M are formed on the front surface 10a side and the communication holes 11h which communicate with the inner walls of the concave portions 11 and the rear surface 10b side and have hole diameters that are smaller than the sizes of the fine particles M are formed is used.

In the collection system according to the present embodiment, the structure is the substrate 10 in which the concave portions 11 that sink so as to be capable of storing the fine particles M are formed on the front surface 10a side and the communication holes 11h which communicate with the inner walls of the concave portions 11 and the rear surface 10b side and have hole diameters that are smaller than the sizes of the fine particles M are formed.

According to the present embodiment, it is possible to produce the flow of intake air which has engulfed the fine particles M between the concave portions 11 and the communication holes 11h in the substrate 10, and thus desired fine particles M can be reliably suctioned. Additionally, the communication holes 11h have hole diameters that are smaller than the sizes of the fine particles M, and thus the fine particles M do not pass through the communication holes 11h, and the fine particles M can be reliably held in the concave portions 11.

In addition, the nozzle location measurement step in the present embodiment includes the nozzle lifting and lowering step of lifting and lowering the nozzle 20 with respect to the substrate 10 in the first direction V1, the substrate moving step of moving the substrate 10 in the second direction V2 after the nozzle lifting and lowering step, and the determination step of determining whether or not the nozzle 20 moves together with the substrate 10 in the substrate moving step.

According to this method, the determination step of determining whether or not the nozzle 20 moves together with the substrate 10 in the substrate moving step is included, and thus, when the nozzle 20 is determined as moving together with the substrate 10 in the determination step, it is possible to assume that the nozzle 20 is in contact with the substrate 10. On the other hand, when the nozzle 20 is determined as not moving together with the substrate 10 in the determination step, it is possible to assume that the nozzle 20 is away from the substrate 10. Therefore, it is possible to move the nozzle 20 as close as possible to the substrate 10 while confirming whether or not the nozzle 20 is actually in contact with the substrate 10. Therefore, it is possible to accurately determine the locations of the substrate 10 and the nozzle 20.

In the location determination of the substrate 10 and the nozzle 20, methods in which an optical sensor is used can also be considered. However, in a case in which the front surface 10a of the substrate 10 is a liquid surface, there is a possibility that it may not be possible to accurately measure the location of the substrate 10 due to the refraction, reflection, and the like of light on the liquid surface. In contrast, according to this method, since light is not used, even in a case in which the front surface 10a of the substrate 10 is a liquid surface, it is possible to accurately determine the locations of the substrate 10 and the nozzle 20.

In addition, in the nozzle lifting and lowering step, since the nozzle 20 is captured using the camera 40 having a focus adjusted to the front surface 10a of the substrate 10, the right focus is obtained when the nozzle 20 is moved close to the front surface 10a of the substrate 10 in the nozzle lifting and lowering step, and thus it is possible to clearly recognize the nozzle 20 using the captured images of the camera 40. Therefore, it is possible to easily move the nozzle 20 close to the front surface 10a of the substrate 10 while viewing the captured images of the camera 40. Therefore, it is possible to accurately and easily determine the locations of the front surface 10a of the substrate 10 and the nozzle 20.

In addition, the nozzle location measurement step in the present embodiment further includes the location-adjusting step of adjusting the relative locations of the nozzle 20 and the substrate 10 on the basis of the determination results in the determination step by moving the nozzle 20 away from the substrate 10 when the nozzle 20 has been determined as moving together with the substrate or resting the nozzle 20 when the nozzle 20 has been determined as not moving together with the substrate.

According to this method, in the location-adjusting step, when the nozzle 20 has been determined as moving together with the substrate on the basis of the determination results in the determination step, the nozzle 20 is moved away from the substrate 10, and thus it is possible to release the state in which the nozzle 20 is in contact with the substrate 10. On the other hand, in the location-adjusting step, when the nozzle 20 has been determined as not moving together with the substrate on the basis of the determination results in the determination step, it is possible to maintain the state in which the nozzle 20 is away from the substrate 10 by resting the nozzle 20. In addition, it is possible to move the nozzle 20 as close as possible to the substrate 10 by adjusting the relative locations of the nozzle 20 and the substrate 10 on the basis of the determination results in the determination step. Therefore, it is possible to more accurately determine the locations of the nozzle 20 and the substrate 10 on the basis of the determination results in the determination step. Additionally, when the nozzle 20 has been determined as moving together with the substrate on the basis of the determination results in the determination step, it is possible to avoid the application of excess loads to the nozzle 20 or the incision of the nozzle 20 into the substrate 10 caused by the contact between the nozzle 20 and the substrate 10 for an excess period of time by moving the nozzle 20 away from the substrate 10.

In addition, the collection system 1 further includes the nozzle location measurement device 30 that measures the location of the nozzle 20 with respect to the substrate 10, and the nozzle location measurement device 30 includes the nozzle-lifting-and-lowering mechanism 31 that lifts and lowers the nozzle 20 with respect to the substrate 10 in the first direction V1, the structure-moving mechanism 35 that moves the substrate 10 in the second direction V2, and the determination portion 39 that determines whether or not the nozzle 20 moves together with the substrate 10 when the substrate 10 is moved in the second direction V2.

According to this constitution, the determination portion 39 that determines whether or not the nozzle 20 moves together with the substrate 10 when the substrate 10 is moved in the second direction V2 is included, and thus, when the nozzle 20 is determined as moving together with the substrate 10 by the determination portion 39, it is possible to assume that the nozzle 20 is in contact with the substrate 10. On the other hand, when the nozzle 20 is determined as not moving together with the substrate 10 by the determination portion 39, it is possible to assume that the nozzle 20 is away from the substrate 10. Therefore, it is possible to move the nozzle 20 as close as possible to the substrate 10 while confirming whether or not the nozzle 20 is actually in contact with the substrate 10. Therefore, it is possible to accurately determine the locations of the substrate 10 and the nozzle 20.

In addition, in the collection system 1, the nozzle location measurement device 30 further includes the camera 40 that captures the nozzle 20 with the focus adjusted to the front surface 10a of the substrate 10.

According to this constitution, the right focus is obtained when the nozzle 20 is moved close to the front surface 10*a* of the substrate 10, and thus it is possible to clearly recognize the nozzle 20 using the captured images of the camera 40. Therefore, it is possible to easily move the nozzle 20 close to the front surface 10*a* of the substrate 10 while viewing the captured images of the camera 40. Therefore, it is possible to accurately and easily determine the locations of the front surface 10*a* of the substrate 10 and the nozzle 20.

In addition, in the present embodiment, the nozzle 20 is formed of a resin or metal.

In a case in which the nozzle 20 is formed of glass, when the nozzle 20 is in contact with the substrate 10 for an excess period of time and excess loads are applied to the nozzle 20, there is a possibility that the nozzle 20 breaks. In contrast, in the present embodiment, since the nozzle 20 is formed of a resin or metal, even when the nozzle 20 is in contact with the substrate 10 for an excess period of time and excess loads are applied to the nozzle 20, the nozzle bends to a certain extent, and thus it is possible to avoid the breakage of the nozzle 20.

Second Embodiment

Hereinafter, a second embodiment of the present invention will be described using FIG. 8.

Figure 8:
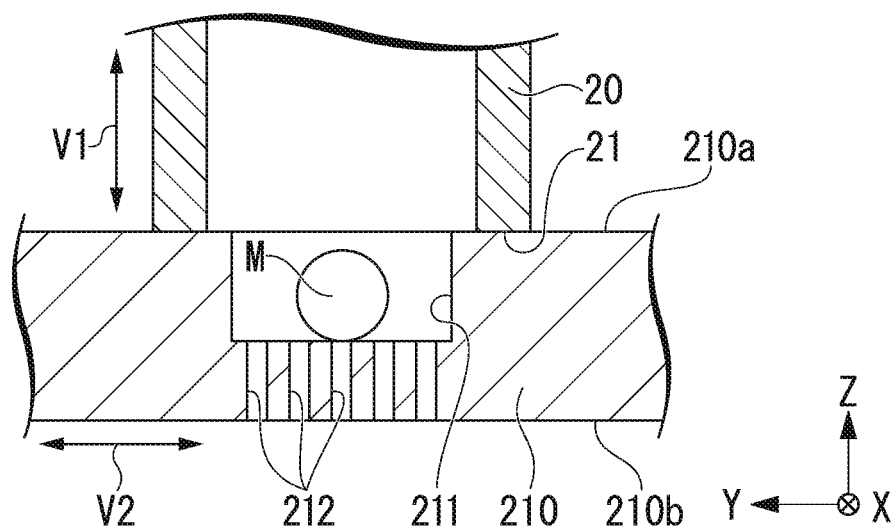
FIG. 8 is a view which corresponds to FIG. 6 and illustrates a main portion of a substrate according to a second embodiment.

FIG. 8 is a view which corresponds to FIG. 6 and illustrates the main portion of a substrate 210 according to the second embodiment.

As illustrated in FIG. 8, the present embodiment is different from the first embodiment with regards to the substrate (structure). In FIG. 8, the same constitutions as in the first embodiment are given the same reference signs and will not be described in detail.

<Substrate (Structure)>

On a front surface 210*a* side (one surface side) of the substrate 210, concave portions 211 that sink so as to be capable of storing the fine particles M are formed. The cross-sectional shape of the concave portion 211 forms a rectangular concave shape. The size of the concave portion 211 may be a size in which only one fine particle M can be stored. Therefore, it is possible to rapidly collect a single kind of target cells or the like. The size of the concave portion 211 may be a size in which a plurality of fine particles M can be stored and is not particularly limited.

In the substrate 210, a plurality of communication holes 212 communicating with bottom walls (inner walls) of the concave portions 211 and a rear surface 210*b* side (the other surface side) is formed. The concave portions 211 and the communication holes 212 communicate spaces storing the fine particles M with one surface side and the other surface side of the substrate 210. The concave portions 211 and the communication holes 212 correspond to the "communication portions". The communication holes 212 linearly extend toward the rear surface 210*b* from the bottom walls of the concave portions 211. The communication holes 212 have hole diameters that are smaller than the sizes of the fine particles M.

The communication holes 212 do not only communicate with the bottom walls of the concave portions 211 and the rear surface 210*b* side but also may communicate side walls of the concave portions 211 and the rear surface 210*b* side. That is, the communication holes 212 need to communicate with the inner walls of the concave portions 211 and the rear surface 210*b* side.

According to the present embodiment, it is possible to produce the flow of intake air which has engulfed the fine particles M between the concave portions 211 and the communication holes 212 in the substrate 210, and thus desired fine particles M can be reliably suctioned. Additionally, the communication holes 212 has hole diameters that are smaller than the sizes of the fine particles M, and thus the fine particles M do not pass through the communication holes 212, and the fine particles M can be reliably held in the concave portions 211.

In the present embodiment, the state in which the tip portion 21 of the nozzle 20 is in contact with the front surface 210*a* of the substrate 210 has been described as an example, but the state is not limited thereto. For example, the interval between the tip portion 21 of the nozzle 20 and the front surface 210*a* of the substrate 210 may be set to be smaller than the size of the fine particle M.

Third Embodiment

Hereinafter, a third embodiment of the present invention will be described using FIG. 9.

Figure 9:
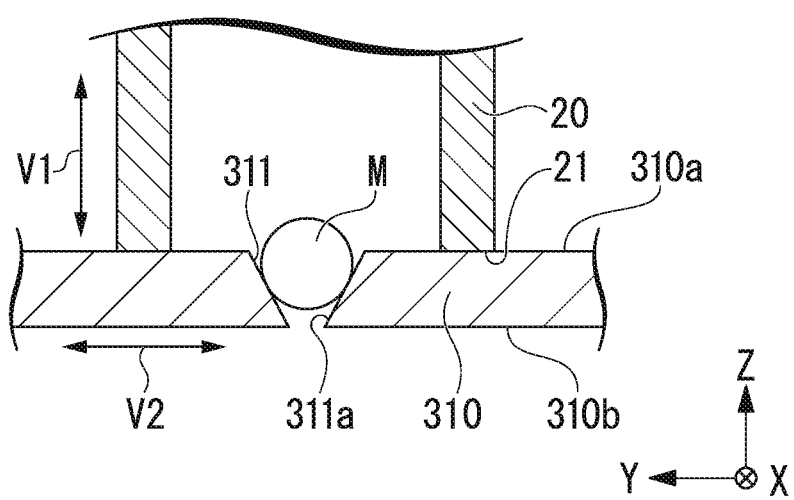
FIG. 9 is a view which corresponds to FIG. 6 and illustrates a main portion of a substrate according to a third embodiment.

FIG. 9 is a view which corresponds to FIG. 6 and illustrates the main portion of a substrate 310 according to the third embodiment.

As illustrated in FIG. 9, the present embodiment is different from the first embodiment with regards to the substrate (structure). In FIG. 9, the same constitutions as in the first embodiment are given the same reference signs and will not be described in detail.

<Substrate (Structure)>

In the substrate 310, through-holes 311 penetrating the substrate so as to be capable of storing the fine particles M are formed. The through-holes 311 communicate spaces storing the fine particles M with one surface side and the other surface side of the substrate 310. The through-holes 311 correspond to the "communication portions". The through-hole 311 has a taper shape that contracts toward a rear surface 310*b* from a front surface 310*a* side. The portion of the through-hole 311 on the rear surface 310*b* side has a hole diameter that is smaller than the size of the fine particle M.

The size of the through-hole 311 is a size in which only one fine particle M can be stored. Therefore, it is possible to rapidly collect a single kind of target cells or the like. The size of the through-hole 311 may be a size in which a plurality of fine particles M can be stored and is not particularly limited.

The inner wall of the through-hole 311 is linearly inclined toward the rear surface 310*b* from the front surface 310*a* side. In the inner wall of the through-hole 311, a support portion 311*a* capable of supporting the fine particle M is formed. The support portion 311*a* is, in the inner wall of the through-hole 311, a portion having a hole diameter that is smaller than the size of the fine particle M.

The inner wall of the through-hole 311 is not only linearly inclined toward the rear surface 310*b* from the front surface 310*a* side but also may be inclined in a curved manner (in a bent manner) toward the rear surface 310*b* from the front surface 310*a* side. In addition, at least a part of the inner wall of the through-hole 311 may be curved. That is, in the inner wall of the through-hole 311, the support portion 311*a* capable of supporting the fine particle M needs to be formed.

As described above, in the collection method for fine particles according to the present embodiment, as the structure, the substrate 310 in which the through-holes 311 penetrating the substrate so as to be capable of storing the fine particles M are formed and the support portions 311*a* capable of supporting the fine particles M are formed in the inner walls of the through-holes 311 is used.

In the collection system according to the present embodiment, the structure is the substrate 310 in which the through-holes 311 penetrating the substrate so as to be capable of storing the fine particles M are formed and the support portions 311a capable of supporting the fine particles M are formed in the inner walls of the through-holes 311.

According to the present embodiment, it is possible to produce the flow of intake air which has engulfed the fine particles M through the through-holes 311 in the substrate 310, and thus desired fine particles M can be reliably suctioned. Additionally, the support portion 311a capable of supporting the fine particle M are formed in the inner walls of the through-holes 311, and thus the fine particles M do not pass through the through-holes 311, and the fine particles M can be reliably held in the support portions 311a.

In the present embodiment, the state in which the tip portion 21 of the nozzle 20 is in contact with the front surface 310a of the substrate 310 has been described as an example, but the state is not limited thereto. For example, the interval between the tip portion 21 of the nozzle 20 and the front surface 310a of the substrate 310 may be set to be smaller than the size of the fine particle M.

Fourth Embodiment

Hereinafter, a fourth embodiment of the present invention will be described using FIG. 10.

Figure 10:
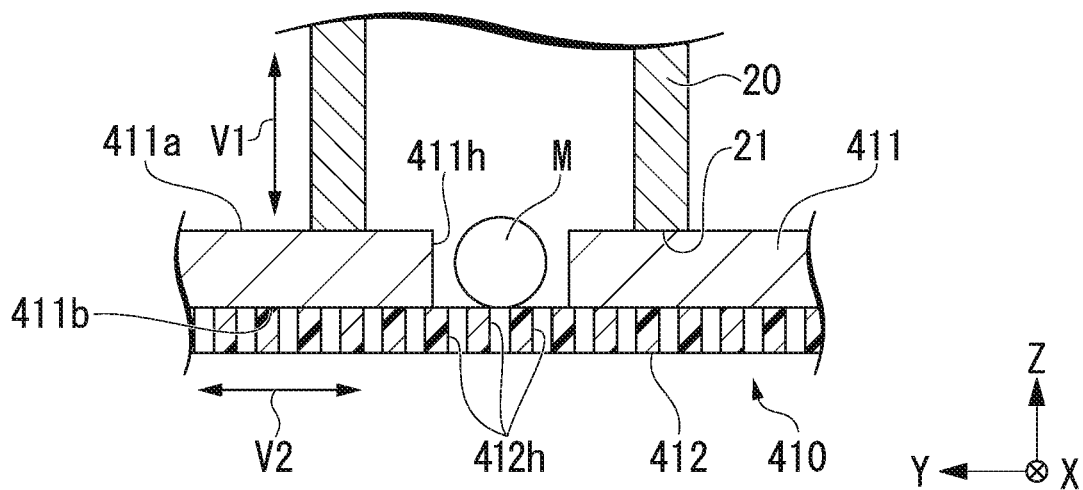
FIG. 10 is a view which corresponds to FIG. 6 and illustrates a main portion of a structure according to a fourth embodiment.

FIG. 10 is a view which corresponds to FIG. 6 and illustrates the main portion of a substrate 410 according to the forth embodiment.

As illustrated in FIG. 10, the present embodiment is different from the first embodiment with regards to the structure. In FIG. 9, the same constitutions as in the first embodiment are given the same reference signs and will not be described in detail.

<Structure>

A structure 410 includes a substrate 411 and a support layer 412.

For example, the substrate 411 is a glass substrate or a plastic substrate. In the substrate 411, through-holes 411h penetrating the substrate so as to be capable of storing the fine particles M are formed. The size of the through-hole 411h is a size in which only one fine particle M can be stored. Therefore, it is possible to rapidly collect a single kind of target cells or the like. The size of the through-hole 411h may be a size in which a plurality of fine particles M can be stored and is not particularly limited.

The support layer 412 is disposed on a rear surface 411b side (the other surface side) of the substrate 411. The support layer 412 is bonded to the rear surface 411b of the substrate 411. For example, the support layer 412 is a resin layer. The thickness of the support layer 412 may be thinner than the thickness of the substrate 411.

In the support layer 412, a plurality of communication holes 412h communicating with the through-holes 411h is formed. The through-holes 411h and the communication holes 412h communicate spaces storing the fine particles M with one surface side and the other surface side of the structure 410. The through-holes 411h and the communication holes 412h correspond to the "communication portions". The plurality of communication holes 412h is disposed in a matrix form along the X-axis direction and the Y-axis direction at certain intervals. The communication holes 412h linearly extend so as to penetrate the support layer 412 in the thickness direction. The communication holes 412h have hole diameters that are smaller than the sizes of the fine particles M. Therefore, the support layer 412 is capable of supporting the fine particles M.

The plurality of communication holes 412h is not only disposed in a matrix form along the X-axis direction and the Y-axis direction at certain intervals but also may be randomly disposed. For example, the support layer 412 may have a random porous structure. That is, in the support layer 412, the communication holes 412h communicating with the through-holes 411h need to be formed.

<Collection Method for Fine Particles>

The collection method for fine particles of the present embodiment includes a collection step of suctioning and collecting the fine particles M from the front surface 411a side (one surface side) of the substrate 411 using the nozzle 20 and the structure 410. For example, before the collection step, the nozzle location measurement step is carried out.

In the collection step, the fine particles M are suctioned and collected using the nozzle 20 in a state in which the tip portion 21 of the nozzle 20 is in contact with the front surface 411a of the substrate 411.

As described above, in the collection method for fine particles according to the present embodiment, as the structure 410, a structure including the substrate 411 in which the through-holes 411h penetrating the structure so as to be capable of storing the fine particles M are formed and the support layer 412 which is disposed on the rear surface 411b side of the substrate 411, has the communication holes 412h that communicate with the through-holes 411h, and is capable of supporting the fine particles M is used.

In the collection system according to the present embodiment, the structure 410 includes the substrate 411 in which the through-holes 411h penetrating the structure so as to be capable of storing the fine particles M are formed and the support layer 412 which is disposed on the rear surface 411b side of the substrate 411, has the communication holes 412h that communicate with the through-holes 411h, and is capable of supporting the fine particles M.

According to the present embodiment, it is possible to produce the flow of intake air which has engulfed the fine particles M between the through-holes 411h in the substrate 411 and the communication holes 412h in the support layer 412, and thus desired fine particles M can be reliably suctioned.

In addition, in the collection step in the present embodiment, the fine particles M are suctioned and collected using the nozzle 20 in a state in which the tip portion 21 of the nozzle 20 is in contact with the front surface 411a of the substrate 411.

According to this method, it is possible to avoid the suction of external foreign substances compared with a case in which the nozzle 20 is away from the front surface 411a of the substrate 411. Therefore, it is possible to avoid contamination with foreign substances and reliably suction desired fine particles M. Additionally, it is possible to produce the flow of intake air which has engulfed the fine particles M only between the through-holes 411h in the substrate 411 and the communication holes 412h in the support layer 412, and it is possible to suppress the suction power of the nozzle 20 at a lower level compared with a case in which the nozzle 20 is away from the front surface 411a of the substrate 411.

In the present embodiment, the state in which the tip portion 21 of the nozzle 20 is in contact with the front surface 411a of the substrate 411 has been described as an example, but the state is not limited thereto. For example, the interval between the tip portion 21 of the nozzle 20 and the front surface 411a of the substrate 411 may be set to be smaller than the size of the fine particle M.

Fifth Embodiment

Hereinafter, a fifth embodiment of the present invention will be described using FIG. 11.

Figure 11:
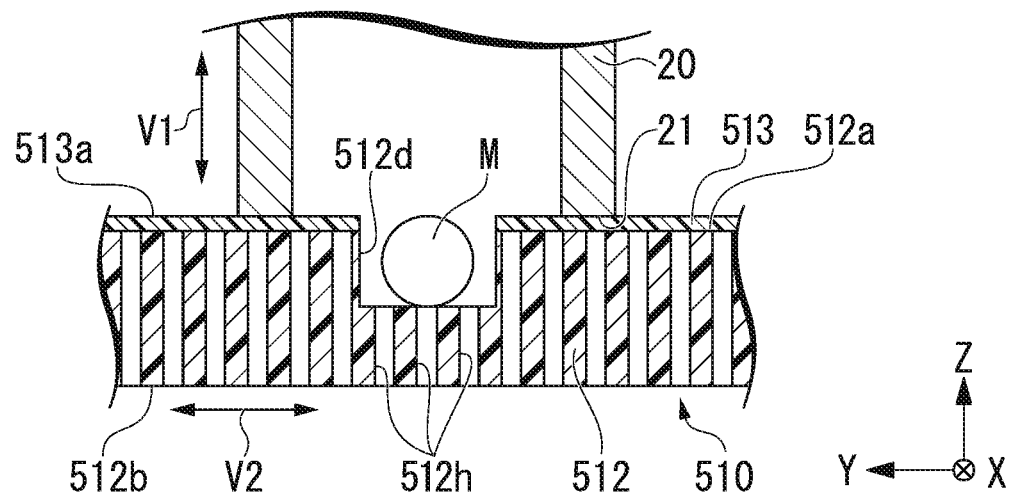
FIG. 11 is a view which corresponds to FIG. 6 and illustrates a main portion of a structure according to a fifth embodiment.

FIG. 11 is a view which corresponds to FIG. 6 and illustrates the main portion of a structure 510 according to the fifth embodiment.

As illustrated in FIG. 11, the present embodiment is different from the first embodiment with regards to the structure. In FIG. 11, the same constitutions as in the first embodiment are given the same reference signs and will not be described in detail.

<Structure>

A structure 510 includes a support layer 512 and a coating layer 513. For example, the support layer 512 is a resin layer. In the support layer 512, concave portions 512d that sink so as to be capable of storing the fine particles M are formed. The cross-sectional shape of the concave portion 512d forms a rectangular concave shape. The size of the concave portion 512d is a size in which only one fine particle M can be stored. Therefore, it is possible to rapidly collect a single kind of target cells or the like. The size of the concave portion 512d may be a size in which a plurality of fine particles M can be stored and is not particularly limited.

In the support layer 512, a plurality of communication holes 512h communicating with the concave portions 512d is formed. The concave portions 512d and the communication holes 512h communicate spaces storing the fine particles M with one surface side and the other surface side of the structure 510. The concave portions 512d and the communication holes 512h correspond to the "communication portions".

The plurality of communication holes 512h is disposed in a matrix form along the X-axis direction and the Y-axis direction at certain intervals. The communication holes 512h linearly extend so as to penetrate the support layer 512 in the thickness direction. The communication holes 512h have hole diameters that are smaller than the sizes of the fine particles M. Therefore, the support layer 512 is capable of supporting the fine particles M.

The plurality of through-holes 512h is not only disposed in a matrix form along the X-axis direction and the Y-axis direction at certain intervals, but may also be randomly disposed. For example, the support layer 512 may have a random porous structure. That is, the communication holes 512h that communicate with the concave portions 512d need to be formed in the support layer 512.

For example, the coating layer 513 is a resin layer. The coating layer 513 covers a front surface 512a (a surface on the concave portion 512d side) of the support layer 512. The coating layer 513 fully covers the front surface 512a of the support layer 512 so that only the concave portions 512d are exposed. The thickness of the coating layer 513 may be thinner than the thickness of the support layer 512.

As described above, in the collection method for fine particles according to the present embodiment, as the structure 510, a structure including the support layer 512 which has the concave portions 512d that sink so as to be capable of storing the fine particles M, has the communication holes 512h that communicate with the concave portions 512d, and is capable of supporting the fine particles M and the coating layer 513 that covers the front surface 512a of the support layer 512 is used.

In the collection system according to the present embodiment, the structure 510 includes the support layer 512 which has the concave portions 512d that sink so as to be capable of storing the fine particles M, has the communication holes 512h that communicate with the concave portions 512d, and is capable of supporting the fine particles M and the coating layer 513 that covers the front surface 512a of the support layer 512.

According to the present embodiment, it is possible to produce the flow of intake air which has engulfed fine particles M between the concave portions 512d and the communication holes 512h in the support layer 512, and thus desired fine particles M can be reliably suctioned. Additionally, the coating layer 513 covers the front surface 512a of the support layer 512, it is possible to suppress the intrusion of foreign substances into the communication holes 512h in the support layer 512.

In the present embodiment, the state in which the tip portion 21 of the nozzle 20 is in contact with the front surface 513a of the coating layer 513 has been described as an example, but the state is not limited thereto. For example, the interval between the tip portion 21 of the nozzle 20 and the front surface 513a of the coating layer 513 may be set to be smaller than the size of the fine particle M.

Sixth Embodiment

Hereinafter, a sixth embodiment of the present invention will be described using FIG. 12 to FIG. 14.

Figure 12:
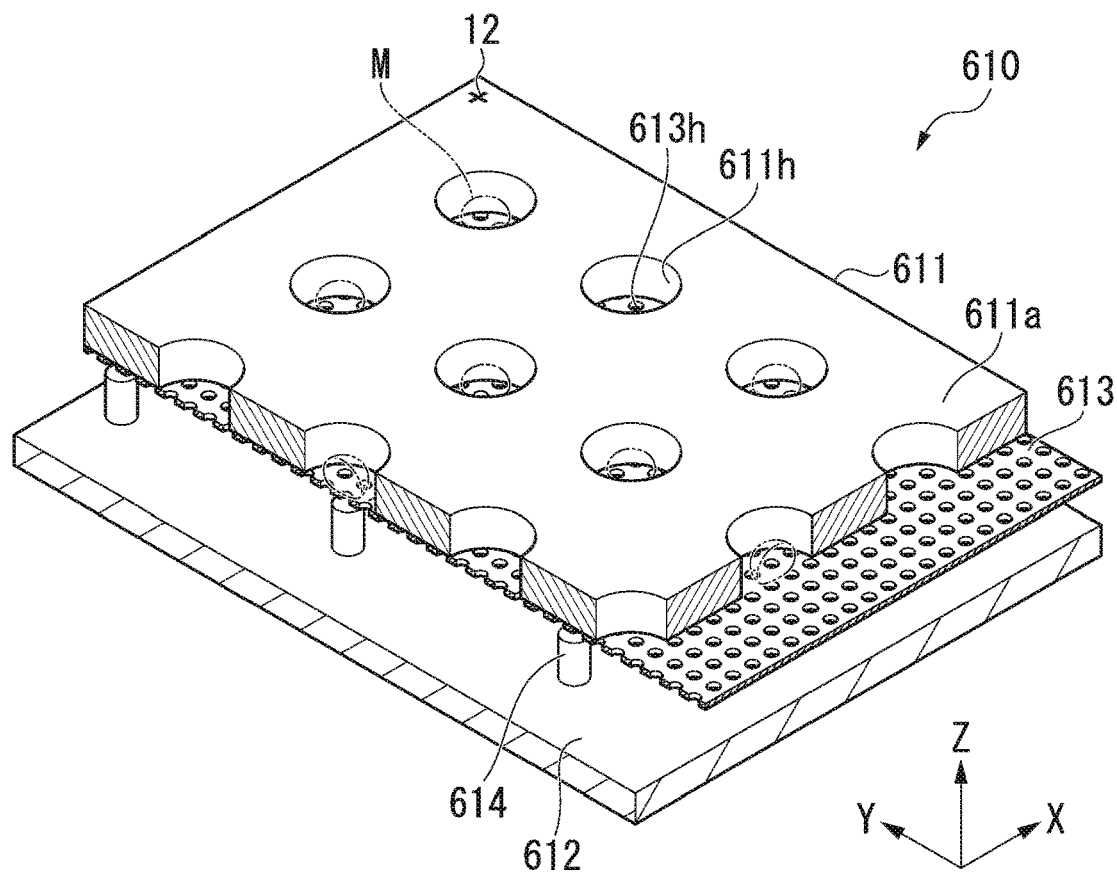
FIG. 12 is a perspective view illustrating a schematic constitution of a structure according to a sixth embodiment.
Figure 13:
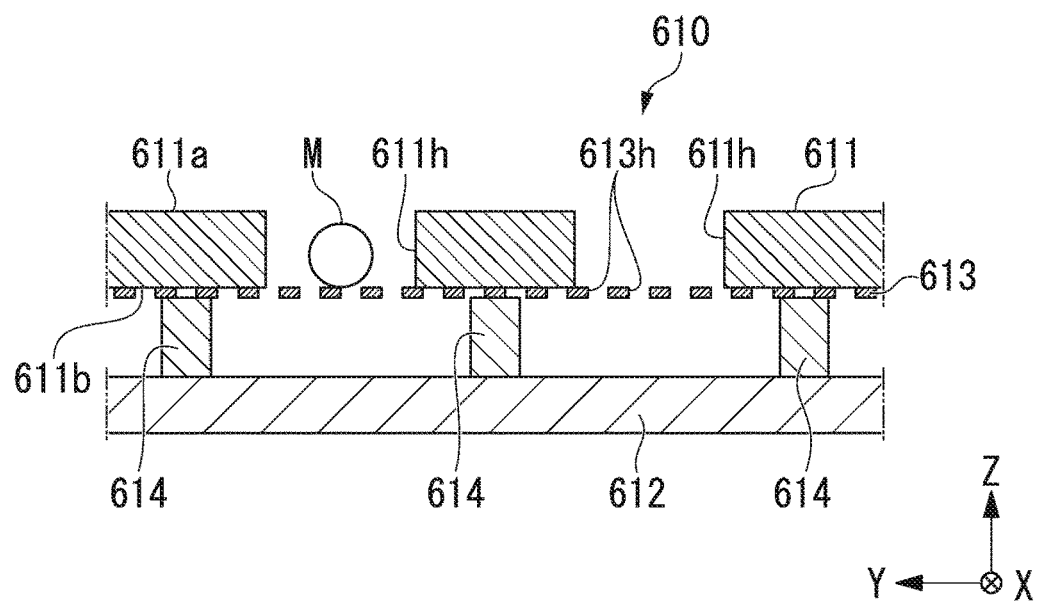
FIG. 13 is a cross-sectional view illustrating a schematic constitution of the structure according to the sixth embodiment.

FIG. 12 is a perspective view illustrating the schematic constitution of a structure 610 according to the sixth embodiment. FIG. 13 is a cross-sectional view illustrating the schematic constitution of the structure 610 according to the sixth embodiment.

As illustrated in FIG. 12, the present embodiment is different from the first embodiment with regards to the structure. In FIG. 12 to FIG. 14, the same constitutions as in the first embodiment are given the same reference signs and will not be described in detail.

<Structure>

The structure 610 has a rectangular shape. For example, the structure 610 has lengths of approximately 50 mm in the X-axis direction and the Y-axis direction. The structure 610 is light-transmissible. The structure 610 includes a first substrate 611, a second substrate 612, a support layer 613, and support columns 614.

<First substrate>

The first substrate 611 has a rectangular sheet shape. For example, the first substrate 611 is a glass substrate or a plastic substrate. For example, the thickness of the first substrate 611 is approximately 5 μm to 100 μm. In a corner portion of a front surface 611a (upper surface) of the first substrate 611, the marking 12 is formed.

In the first substrate 611, a plurality of through-holes 611h penetrating the substrate so as to be capable of storing the fine particles M is formed. The plurality of through-holes 611h is disposed in a matrix form along the X-axis direction and the Y-axis direction at certain intervals. In a plan view, the through-hole 611h has a circular shape. The size of the through-hole 611h may be a size in which only one fine particle M can be stored. Therefore, it is possible to rapidly collect a single kind of target cells or the like. The size of the through-hole 611h may be a size in which a plurality of fine particles M can be stored and is not particularly limited.

In the respective through-holes 611h, a culture solution is stored together with the fine particles M. Examples of the culture solution include DMEM culture media, MEM culture media, RPMI 1640 culture media, Fischer's culture media, and the like. The kind of culture solution is not particularly limited.

<Second substrate>

The second substrate 612 faces the first substrate 611 through the support layer 613 and the support columns 614.

The second substrate 612 has a rectangular sheet shape. For example, the second substrate 612 is a glass substrate or a plastic substrate.

<Support layer>

The support layer 613 is disposed between the first substrate 611 and the second substrate 612. Specifically, the support layer 613 is bonded to a rear surface 611b (lower surface) of the first substrate 611. For example, the support layer 613 is a resin layer. The thickness of the support layer 613 may be thinner than the thickness of the first substrate 611.

In the support layer 613, a plurality of communication holes 613h communicating with the through-holes 611h is formed. The through-holes 611h and the communication holes 613h communicate spaces storing the fine particles M with one surface side and the other surface side of the structure 610. The through-holes 611h and the communication holes 613h correspond to the "communication portions". The plurality of communication holes 613h is disposed in a matrix form along the X-axis direction and the Y-axis direction at certain intervals. The support layer 613 has a mesh shape. In a plan view, the communication hole 613h has a circular shape. The diameter of the communication hole 613h is smaller than that of the through-holes 611h. The diameter of the communication hole 613h is smaller than the size of the fine particle M. Therefore, the support layer 613 is capable of supporting the fine particles M.

<Support column>

The support columns 614 are disposed between the first substrate 611 and the second substrate 612. The support column 614 has a cylindrical shape that extends in the Z-axis direction. For example, the support column 614 is made of a resin. The support columns 614 couple the first substrate 611 and the second substrate 612 at locations that do not overlap the through-holes 611h.

Figure 14:
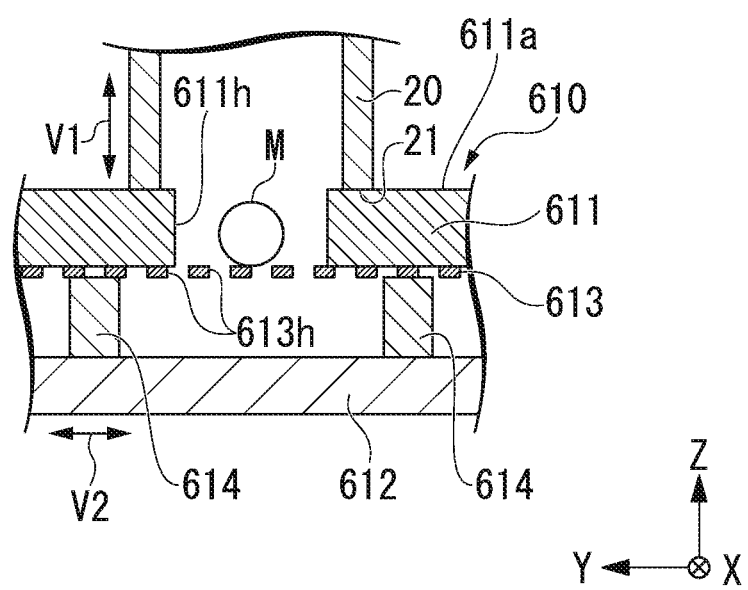
FIG. 14 is a view illustrating a state in which the tip portion of the nozzle is in contact with a front surface of a first substrate.

FIG. 14 is a view illustrating a state in which the tip portion 21 of the nozzle 20 is in contact with a front surface 611a of the first substrate 611.

As illustrated in FIG. 14, in the present embodiment, at the suction position P1, the tip portion 21 of the nozzle 20 is in contact with a surface of the first substrate 611 on a side opposite to the support layer 613 (that is, the front surface 611a). That is, in the nozzle location measurement step in the present embodiment, the tip portion 21 of the nozzle 20 is brought into contact with (adhered to) the front surface 611a of the first substrate 611 in the location-adjusting step.

As described above, in the collection system 601 according to the present embodiment, the structure 610 includes the first substrate 611 in which the through-holes 611h penetrating the substrate so as to be capable of storing the fine particles M are formed, the second substrate 612 facing the first substrate 611, and the support layer 613 which is disposed between the first substrate 611 and the second substrate 612, has the communication holes 613h that communicate with the through-holes 611h, and is capable of supporting the fine particles M.

According to this constitution, it is possible to produce the flow of intake air which has engulfed the fine particles M between the through-holes 611h in the first substrate 611 and the communication holes 613h in the support layer 613. Therefore, desired fine particles M can be reliably collected.

In addition, in the collection system 601, the nozzle 20 is in contact with the front surface 611a of the first substrate 611.

According to this constitution, it is possible to avoid the suction of external foreign substances compared with a case in which the nozzle 20 is away from of the first substrate 611. Therefore, it is possible to avoid contamination with foreign substances and reliably suction desired fine particles M. Additionally, it is possible to produce the flow of intake air which has engulfed the fine particles M only between the through-holes 611h in the first substrate 611 and the communication holes 613h in the support layer 613, and it is possible to suppress the suction power of the nozzle 20 at a lower level compared with a case in which the nozzle 20 is away from the first substrate 611.

In the present embodiment, the state in which the tip portion 21 of the nozzle 20 is in contact with the front surface 611a of the first substrate 611 has been described as an example, but the state is not limited thereto. For example, the interval between the tip portion 21 of the nozzle 20 and the front surface 611a of the first substrate 611 may be set to be smaller than the size of the fine particle M.

In addition, in the present embodiment, an example in which the structure 610 includes the support columns 614 has been described, but the constitution is not limited thereto. For example, the structure 610 may not include the support columns 614. That is, the structure 610 may include the first substrate 611, the second substrate 612, and the support layer 613.

Modification Examples of Structure According to Sixth Embodiment

Modification examples of the structure 610 according to the sixth embodiment will be described using FIG. 15 to FIG. 18.

FIG. 15 to FIG. 18 are perspective views illustrating modification examples of the structure 610.

As illustrated in FIG. 15 to FIG. 18, the present modification examples are different from the structure 610 according to the sixth embodiment with regards to the support layer 613. In FIG. 15 to FIG. 18, the same constitutions as in the sixth embodiment are given the same reference signs and will not be described in detail.

Figure 15:
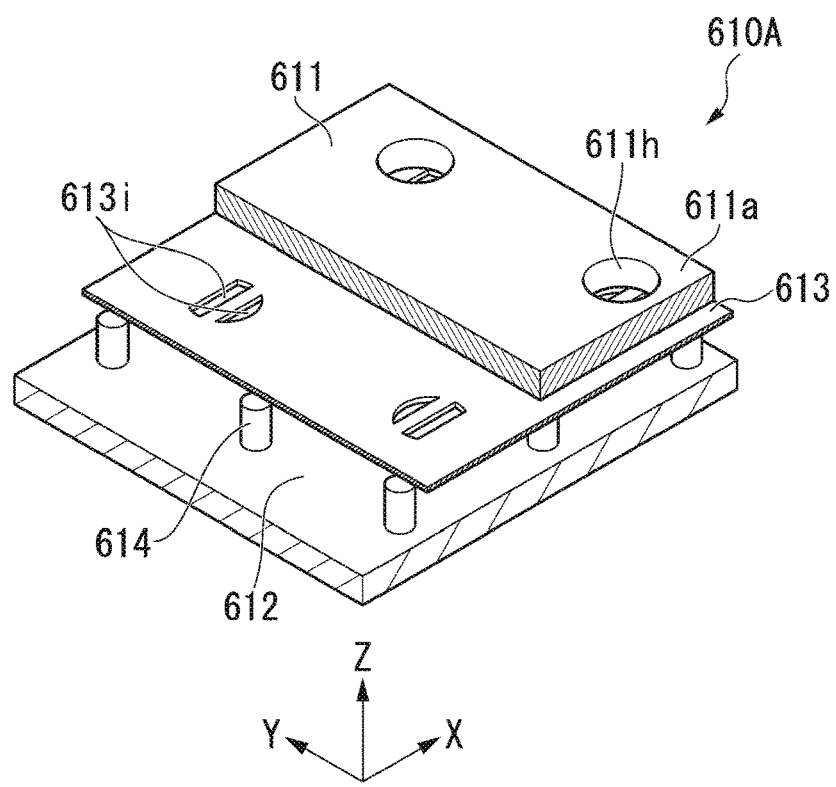
FIG. 15 is a perspective view illustrating a modification example of the structure according to the sixth embodiment.

As illustrated in FIG. 15, in a structure 610A of the present modification example, a plurality of communication holes 613i communicating with the through-holes 611h is formed in the support layer 613. The plurality of communication holes 613i is disposed only in portions in which the communication holes overlap the through-holes 611h in the Z-axis direction. In a plan view, the communication hole 613i has a slit shape (specifically, a shape in which one rectangular shape and one semicircular shape are arranged).

Figure 16:
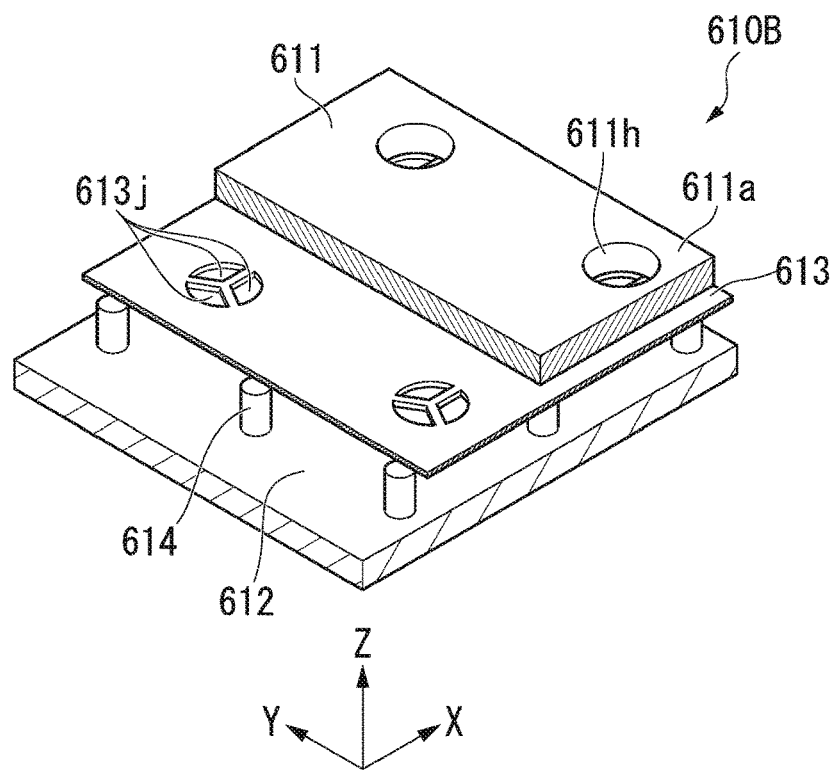
FIG. 16 is a perspective view illustrating a modification example of the structure according to the sixth embodiment.

As illustrated in FIG. 16, in a structure 610B of the present modification example, a plurality of communication holes 613j communicating with the through-holes 611h is formed in the support layer 613. The plurality of communication holes 613j is disposed only in portions in which the communication holes overlap the through-holes 611h in the Z-axis direction. In a plan view, the communication hole 613j has a shape in which three fan-shaped holes having a central angle of approximately 120 degrees are arranged in the circumferential direction.

Figure 17:
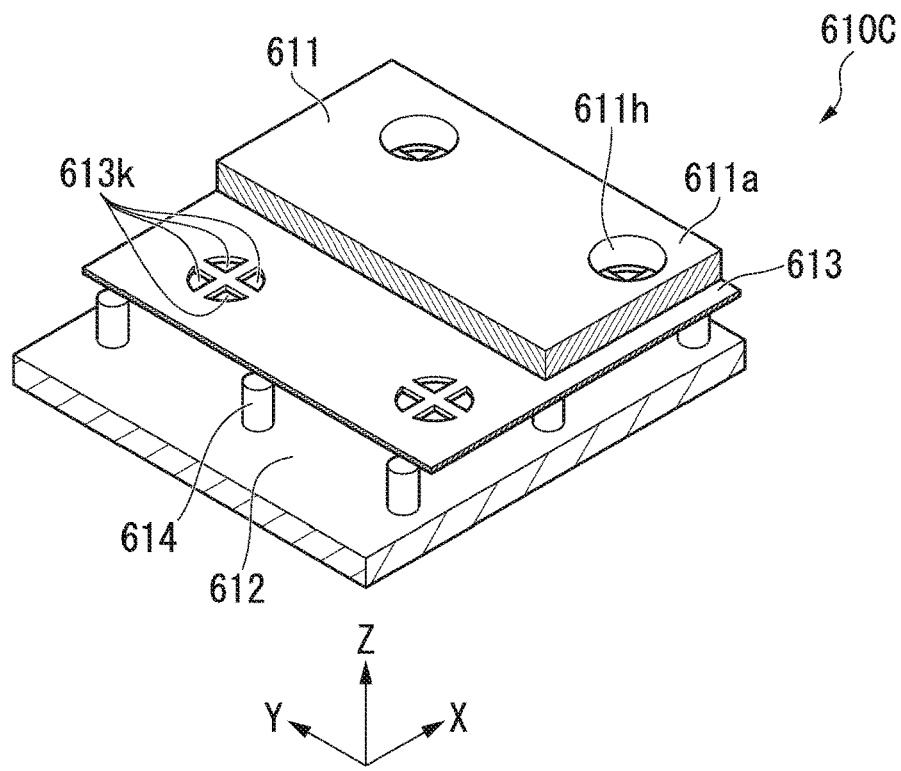
FIG. 17 is a perspective view illustrating a modification example of the structure according to the sixth embodiment.

As illustrated in FIG. 17, in a structure 610C of the present modification example, a plurality of communication holes 613k communicating with the through-holes 611h is formed in the support layer 613. The plurality of communication holes 613k is disposed only in portions in which the communication holes overlap the through-holes 611h in the Z-axis direction. In a plan view, the communication hole 613k has a shape in which four fan-shaped holes having a central angle of approximately 90 degrees are arranged in the circumferential direction.

Figure 18:
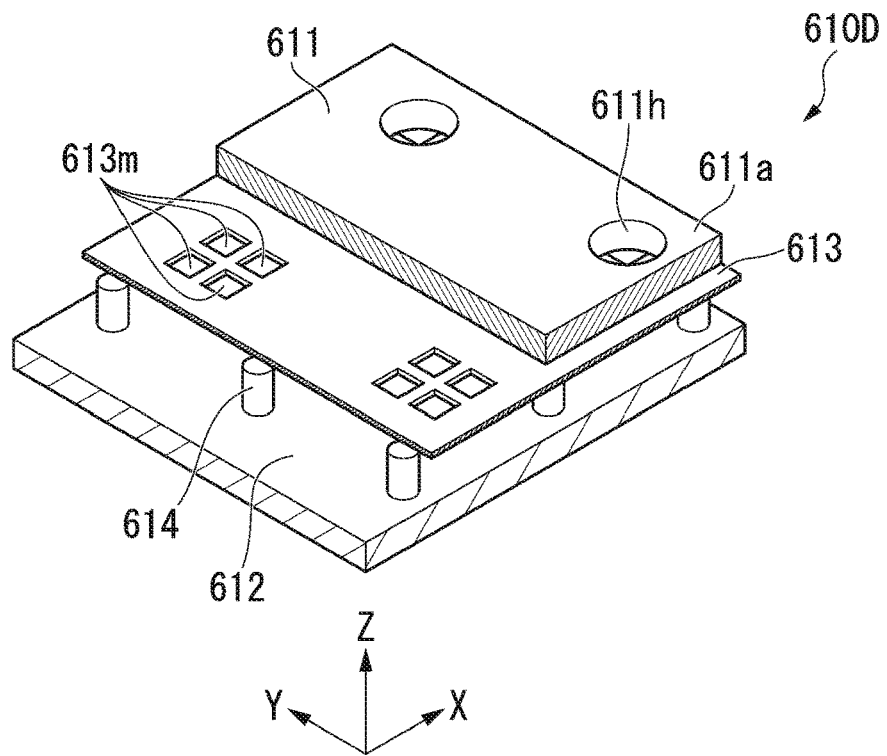
FIG. 18 is a perspective view illustrating a modification example of the structure according to the sixth embodiment.

As illustrated in FIG. 18, in a structure 610D of the present modification example, a plurality of communication holes 613m communicating with the through-holes 611h is formed in the support layer 613. The plurality of communication holes 613m is disposed only in portions in which the communication holes overlap the through-holes 611h in the Z-axis direction. In a plan view, the communication hole 613m has a shape in which four square holes are arranged in the circumferential direction.

The aspects of the support layer 613 (the aspects of the communication hole) are not limited to the examples illustrated in FIG. 15 to FIG. 18, and a variety of aspects can be employed.

Seventh Embodiment

Hereinafter, a seventh embodiment of the present invention will be described using FIG. 19 to FIG. 21.

Figure 19:
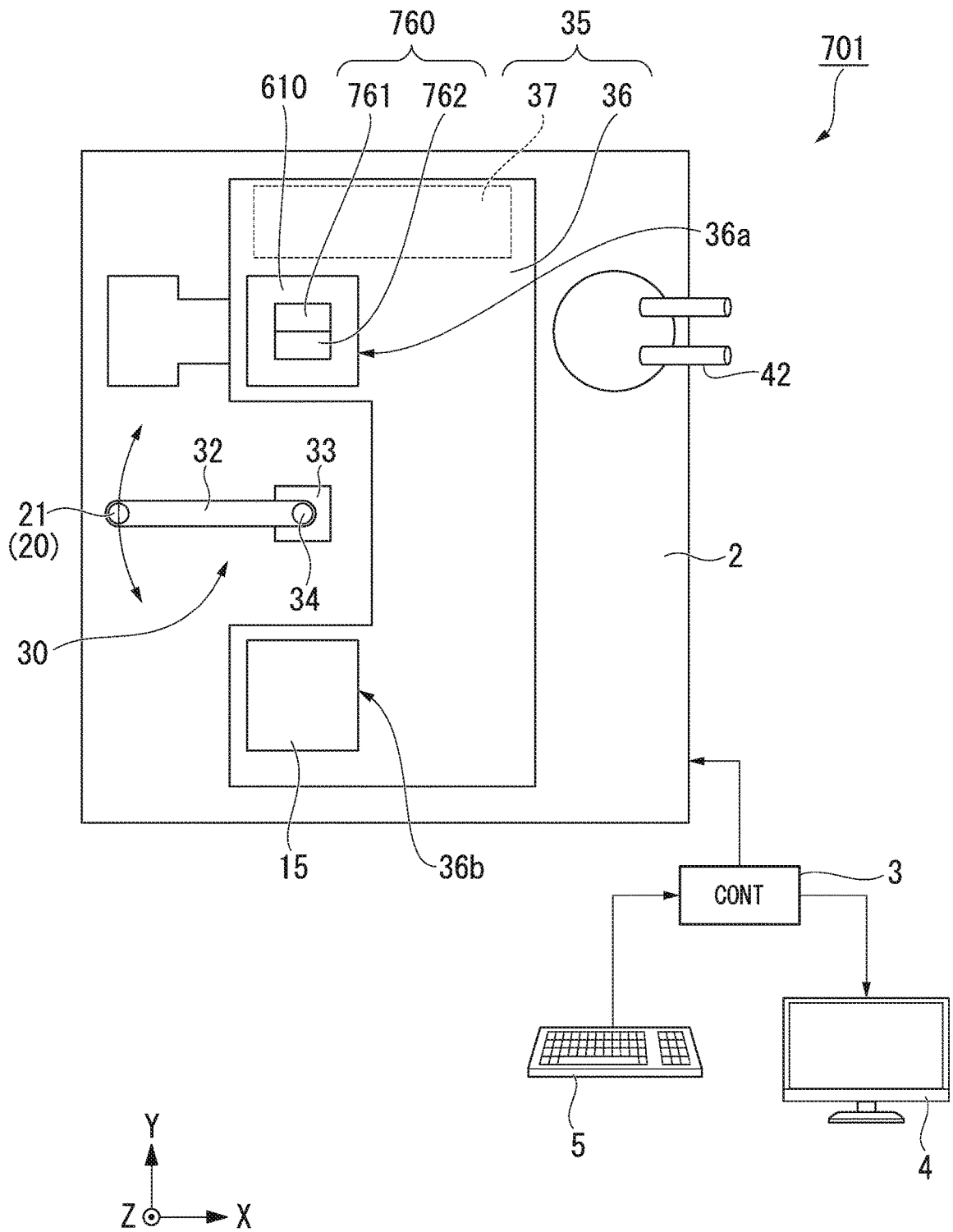
FIG. 19 is a plan view illustrating a schematic constitution of a collection system according to a seventh embodiment.

FIG. 19 is a plan view illustrating the schematic constitution of a collection system 701 according to the seventh embodiment.

As illustrated in FIG. 19, the present embodiment is different from the sixth embodiment in terms of a detection device 760 being further provided. In FIG. 19 to FIG. 21, the same constitutions as in the sixth embodiment are given the same reference signs and will not be described in detail.

<Detection Device>

As illustrated in FIG. 19, in a plan view, the detection device 760 is disposed at a location in which the detection device overlaps the suction and collection region 36a. The detection device 760 includes a first detection device 761 and a second detection device 762.

Figure 20:
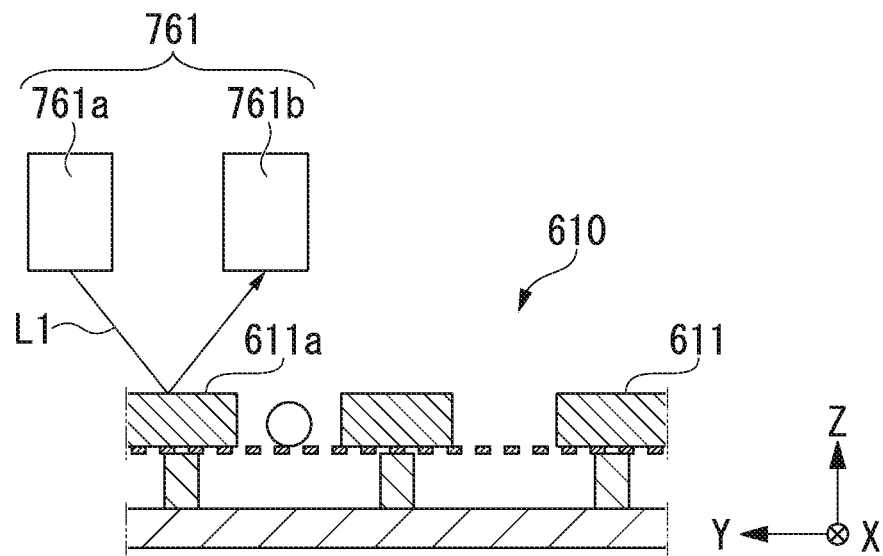
FIG. 20 is a view illustrating a schematic constitution of a first detection device.

FIG. 20 is a view illustrating the schematic constitution of the first detection device 761.

As illustrated in FIG. 20, the first detection device 761 is capable of measuring the height and parallelism of the front surface 611a of the first substrate 611 in a non-contact manner using laser light as detection light. The first detection device 761 is fixed to the base 2 (refer to FIG. 19) using a non-illustrated fixing member. Therefore, the relative location of the first detection device 761 is fixed with respect to the structure 610 mounted on the stage 36. Therefore, the first detection device 761 is capable of highly accurate measurement.

The first detection device 761 includes a light-emitting portion 761a emitting detection light L1, a light reception portion 761b receiving the detection light L1. For example, the light-emitting portion 761a emits laser light having a light diameter of 1 μm as the detection light L1. The light reception portion 761b receives the detection light L1 which has been emitted from the light-emitting portion 761a and reflected by the front surface 611a of the first substrate 611.

For example, the light-emitting portion 761a is a YAG laser. The light reception portion 761b acquires information regarding the height (the coordinate location in the Z-axis direction) and parallelism of the first substrate 611 on the basis of the time taken for the detection light L1 to be reflected by the front surface 611a of the first substrate 611 and reach the light reception portion 761b, the reflection angle of the detection light L1 by the front surface 611a of the first substrate 611, and the like. The first detection device 761 outputs detection results to the control device 3.

Figure 21:
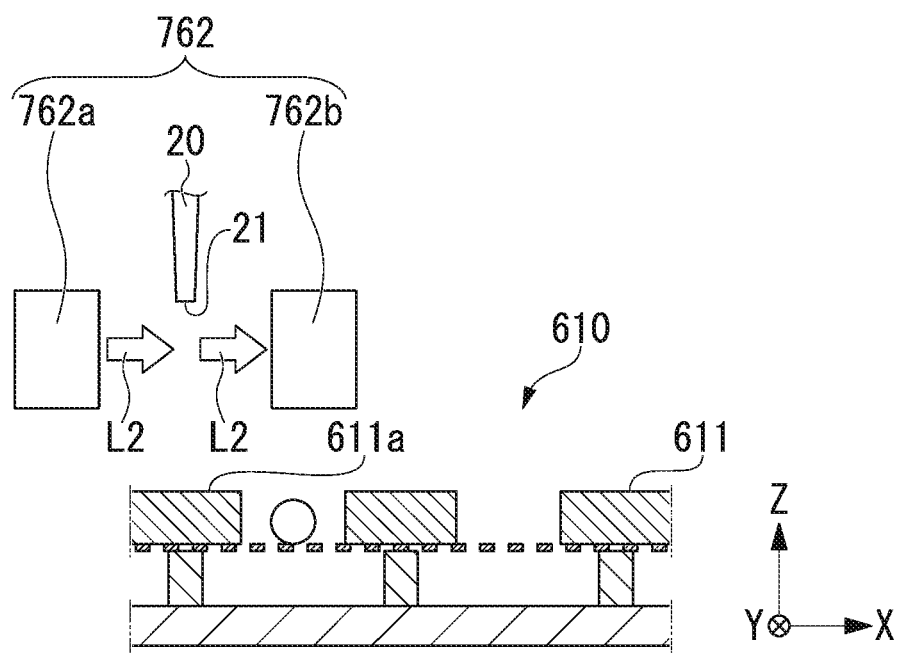
FIG. 21 is a view illustrating a schematic constitution of a second detection device.

FIG. 21 is a view illustrating the schematic constitution of the second detection device 762.

As illustrated in FIG. 21, the second detection device 762 is capable of measuring the height of the tip portion 21 of the nozzle 20 in a non-contact manner using laser light as detection light. The second detection device 762 is fixed to the base 2 (refer to FIG. 19) using a non-illustrated fixing member. Therefore, the relative location of the second detection device 762 is fixed with respect to the nozzle 20. Therefore, the second detection device 762 is capable of highly accurate measurement.

Additionally, the second detection device 762 is capable of moving between measurement locations and waiting locations. For example, in a case in which the nozzle 20 is not detected using the second detection device 762, the second detection device 762 is retreated to a waiting location above the arm 32, thereby preventing the second detection device from hindering the operation of the nozzle 20.

The second detection device 762 includes a light-emitting portion 762a emitting detection light L2, a light reception portion 762b receiving the detection light L2. For example, the light-emitting portion 762a emits laser light having a light diameter of 1 μm as the detection light L2. The light reception portion 762b receives the detection light L2 which has been emitted from the light-emitting portion 762a.

For example, the light-emitting portion 762a is a YAG laser. The light reception portion 762b acquires information regarding the height (the coordinate location in the Z-axis direction) of the tip portion 21 of the nozzle 20 on the basis of the light reception amount (brightness) of the detection light L2 which varies due to the blocking of the detection light L2 emitted from the light-emitting portion 762a by the tip portion 21 of the nozzle 20, and the like. The second detection device 762 outputs detection results to the control device 3.

As described above, the collection system 701 according to the present embodiment includes the first detection device 761 and the second detection device 762 and is thus capable of detecting information regarding the heights of the first substrate 611 and the tip portion 21 of the nozzle 20 in a non-contact manner. Therefore, it is possible to highly accurately detect the location information of the first substrate 611 and the nozzle 20 without causing damage accompanied by the contact between the first substrate 611 and the nozzle 20 and locational deviation accompanied by the contact.

The first detection device 761 does not detect the entire region of the front surface 611a of the first substrate 611. Therefore, it is also assumed that slight protrusions and recesses are generated in some regions (regions outside the detection area) of the front surface 611a for some reasons. Therefore, operators may be enabled to add several micrometers of a margin to the data using the input device 5 (for example, a keyboard). In this case, data obtained by adding a predetermined margin to the height data of the front surface 611a of the first substrate 611 detected by the first detection device 761 can be set as the height of the first front surface 611a.

The present invention is not limited to the above-described embodiments and can be appropriately modified within the scope of the gist of the invention. For example, in the embodiments, examples in which a plurality of concave portions and a plurality of through-holes are formed in a substrate (structure) have been described, but the constitution is not limited thereto. For example, only one concave portion or only one through-hole may be formed in a substrate (structure). That is, the substrate (structure) may be capable of storing only one fine particle M.

In addition, in the embodiments, examples in which the XY alignment is visually carried out have been described, but the constitution is not limited thereto. For example, the XY alignment may be automatically carried out using the marking 12 as a reference. For example, the control device 3 may carry out the XY alignment so that the substrate (structure) and the nozzle 20 match each other in the X-axis direction and the Y-axis direction by controlling the XY driving mechanism 37.

The respective constituent elements described as the embodiments or modification examples thereof in the above description can be appropriately combined within the scope of the gist of the present invention, and it is also possible not to use some constituent elements of a plurality of combined constituent elements appropriately.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

EXPLANATION OF REFERENCES 1, 601, 701 . . . collection system
10, 210, 310 . . . substrate (structure)
10$a$ . . . front surface
11$h$ . . . communication hole
11, 211 . . . concave portion
20 . . . nozzle
212 . . . communication hole
311 . . . through-hole
311$a$ . . . support portion
410, 510, 610, 610A, 610B, 610C, 610D . . . structure
411 . . . substrate
411$h$ . . . through-hole
412 . . . support layer
412$h$ . . . communication hole
512 . . . support layer
512$d$ . . . concave portion
512$h$ . . . communication hole
513 . . . coating layer
611 . . . first substrate
611$h$ . . . through-hole
612 . . . second substrate
613 . . . support layer
613$h$, 613$i$, 613$j$, 613$k$, 613$m$ . . . through-hole
H1 . . . size of fine particle
H2 . . . interval between nozzle and structure
M . . . fine particle

What is claimed is:

1. A method for collecting a fine particle stored in a structure by suctioning the fine particle using a nozzle, wherein, as the structure, a structure in which at least one communication portion that communicates a space storing the fine particle with one surface side and the other surface side of the structure is formed is used, and wherein the structure comprises:

a support layer which has at least one recessed portion formed on one surface of the support layer, and which has a plurality of communication holes that penetrate the support layer in a thickness, wherein some of the plurality of communication holes are positioned within the recessed portion, wherein the recessed portion is capable of storing the fine particle, and a vertical cross-sectional shape of the recessed portion is rectangular, and a coating layer that covers the surface of the support layer on the recessed portion side, so that only the recessed portion is exposed.

2. The method according to claim 1, wherein a hole diameter of the recessed portion is smaller than the size of the fine particle.

3. The method according to claim 1, wherein the fine particle is suctioned and collected using the nozzle in a state in which the nozzle is in contact with one surface of the structure.

* * * * *